United States Patent
Danglas et al.

(10) Patent No.: US 11,918,613 B2
(45) Date of Patent: Mar. 5, 2024

(54) BACTERIOPHAGE THERAPY

(71) Applicants: FERRING B.V., Hoofddorp (NL); INSTITUT PASTEUR, Paris (FR)

(72) Inventors: Pascal Danglas, Saint-Prex (CH); Laurent Debarbieux, Paris (FR)

(73) Assignees: FERRING B.V., Hoofddorp (NL); INSTITUT PASTEUR, Paris (FR)

( * ) Notice: Subject to any disclaimer, the term of this patent is extended or adjusted under 35 U.S.C. 154(b) by 324 days.

(21) Appl. No.: 17/353,337

(22) Filed: Jun. 21, 2021

(65) Prior Publication Data

US 2021/0386805 A1 Dec. 16, 2021

Related U.S. Application Data

(62) Division of application No. 14/787,581, filed as application No. PCT/EP2014/058840 on Apr. 30, 2014, now Pat. No. 11,040,078.

(30) Foreign Application Priority Data

Apr. 30, 2013 (EP) ..................................... 13305568

(51) Int. Cl.
*A61K 35/76* (2015.01)
*A61K 9/00* (2006.01)
*C12N 7/00* (2006.01)

(52) U.S. Cl.
CPC ............ *A61K 35/76* (2013.01); *A61K 9/0053* (2013.01); *C12N 7/00* (2013.01); *C12N 2795/10021* (2013.01); *C12N 2795/10132* (2013.01); *C12N 2795/10171* (2013.01); *Y02A 50/30* (2018.01)

(58) Field of Classification Search
CPC ........ A61K 9/0053; A61K 35/76; C12N 7/00; C12N 2795/10171; A61P 1/12; A61P 1/04; A61P 1/00; Y02A 50/30
See application file for complete search history.

(56) References Cited

U.S. PATENT DOCUMENTS 11,040,078 B2  6/2021  Danglas et al.

FOREIGN PATENT DOCUMENTS

| EP | 2 377 883 A1 | 10/2011 |
|----|----|----|
| WO | WO 01/93904 A1 | 12/2001 |
| WO | WO 02/11549 A2 | 2/2002 |
| WO | WO 2012/036580 A2 | 3/2012 |
| WO | WO 2013/045863 A1 | 4/2013 |

OTHER PUBLICATIONS

Villegas et al. The genome and proteome of a virulent *Escherichia coli* O157:H7 bacteriophage closely resembling *Salmonella* phage Felix O1. (Virology Journal (2009), 6:41. (Year: 2009).*

International Search Report dated Oct. 8, 2014 in application No. PCT/EP2014/058840.
Dogan et al., "Multidrug Resistance is Common in *Escherichia coli* Associated with Ileal Crohn's Disease," Inflamm. Bowel Dis., vol. 19, No. 1, pp. 141-150, Jan. 2013.
Sheng et al., "Application of Bacteriophages to Control Intestinal *Escherichia coli* O157:H7 Levels in Ruminants," Applied and Environmental Microbiology, vol. 72, No. 8, pp. 5359-5366, Aug. 2006.
Wegrzyn et al., "Modulation of the susceptibility of intestinal bacteria to bacteriophages in response to Ag43 phase variation—a hypothesis," Medical Science Monitor: International Journal of Experimental and Clinical Research, vol. 8, No. 6, pp. HY15-HY18, Jun. 2002.
Luslak-Szelachowska et al., "*Escherichia coli* bacteriophages in human stool of patients with gastrointestinal tract diseases," Gastroenterologia Polska, vol. 15, No. 2, pp. 87-90, 2008.
Rolhion, "Adherent-Invasive *Escherichia coli* in Inflammatory Bowel Disease," Inflamm. Bowel Dis., vol. 13, No. 10, pp. 1277-1283, Oct. 2007.
Maura et al., "Intestinal colonization by enteroaggreagative *Escherichia coli* supports long-term bacteriophage replication in mice," Environmental Microbiology, vol. 14, No. 8, pp. 1844-1854, Aug. 2012.
Murugananthan et al., "Clinical Risk Factors for Crohn's Disease Postoperative Recurrence are Reflected in Alterations in Mucosally Adherent Microbiota at Surgical Resection," Gastroenterology, vol. 142, No. 5, Suppl. 1, p. S679, May 2012.
Bringer et al, "The Crohn's disease-associated adherent-invasive *Escherichia coli* strain LF82 replicates in mature phagolysosomes within J774 macrophages," Cell Microbiol., vol. 8, No. 3, pp. 471-484, Mar. 2006 (Abstract).
Brüssow, "Phage Therapy: the Western Perspective," Bacteriophage, McGrath et al., eds., Chapter 6, pp. 59-192, 2007.
Brüssow, "Bacteriophage Therapy: Potential and Problems," Pathogenesis, pp. 267-273, 2009.
Carvalho et al., "Crohn's disease adherent-invasive *Escherichia coli* colonize and induce strong gut inflammation in transgenic mice expressing human CEACAM," The Journal of Experimental Medicine, vol. 206, No. 10, pp. 2179-2189, Sep. 2009.
Chibani-Chennoufi et al., "In Vitro and In Vivo Bacteriolytic Activities of *Escherichia coli* Phages: Implications for Phage Therapy," Antimicrobial Agents and Chemotherapy, vol. 48, No. 7, pp. 2558-2569, Jul. 2004.
Darfeuille-Michaud et al., "Presence of Adherent *Escherichia coli* Strains Ileal Mucosa of Patients With Crohn's Disease," Gastroenterology, vol. 115, No. 6, pp. 1405-1413, Dec. 1998.

(Continued)

*Primary Examiner* — Sean C. Barron
(74) *Attorney, Agent, or Firm* — Foley & Lardner LLP

(57) ABSTRACT

The subject invention provides a pharmaceutical composition comprising: (i) at least one bacteriophage strain(s) capable of producing a lytic infection in an adherent-invasive *Escherichia coli* strain; and (ii) a pharmaceutically acceptable carrier; for the treatment of inflammatory bowel disease. The subject invention further provides a method of treating inflammatory bowel disease comprising administering to a subject in need thereof at least one bacteriophage strain capable of producing a lytic infection in an adherent-invasive *Escherichia coli* strain thereby treating the subject. The subject invention also provides new bacteriophage strains.

10 Claims, No Drawings

Specification includes a Sequence Listing.

(56) References Cited

OTHER PUBLICATIONS

Darfeuille-Michaud et al., "High Prevalence of Adherent-Invasive *Escherichia coli* Associated with Ileal Mucosa in Crohn's Disease," vol. 127, pp. 412-421, Aug. 2004.

Darfeuille-Michaud, "Adherent-invasive *Escherichia coli*: a putative new *E. coli* pathotype associated with Crohn's disease," Int. J. Med. Microbiol., vol. 292, pp. 185-193, 2002.

Gorski et al., "Bacteriophages in Medicine," Bacteriophage, McGrath et al., eds., Chapter 5, pp. 125-158, 2007.

Kutter, "Bacteriphage Therapy: Past and Present," Pathogenesis, pp. 258-266, 2009.

Kutter et al., Phage Therapy in Clincial Practice: Treatment of Human Infections, Current Pharmaceutical Biotechnology, vol. 11, pp. 69-86, 2010.

Lepage et al., "Dysbiosis in inflammatory bowel disease: a role for bacteriophages?," Gut, vol. 57, pp. 424-425, 2008.

Maura et al., "Intestinal colonization by enteroaggregative *Escherichia coli* supports long-term bacteriophage replication in mice," Environmental Microbiology, pp. 1-11, 2011.

Merril et al., "The prospect for bacteriophage therapy in Western medicine," Nature Reviews, vol. 2, pp. 489-497, Jun. 2003.

Reyes et al., "Viruses in the faecal microbiota of monozygotic twins and their mothers," Nature, vol. 466, pp. 334-338, Jul. 2010.

Stone, "Stalin's Forgotten Cure," Science, vol. 298, pp. 728-731, Oct. 2002.

Sulakvelidze et al., "Bacteriophage Therapy in Humans," Bacteriophages—Biology and Applications, Chapter 14, pp. 381-436, 2004.

Villegas et al., "The genome and proteome of a virulent *Escherichia coli* O157:H7 bacteriophage closely resembling *Salmonella* phage Felix OI," Virology Journal, vol. 6, No. 41, pp. 1-5, Apr. 2009.

Wine et al., "Adherent-invasive *Escherichia coli*, strain LF82 disrupts apical junctional complexes in polarized epithelia," BMC Microbiology, vol. 9, No. 180, pp. 1-7, Aug. 2009.

Zuber et al., "Genome Analysis of Phage JS98 Defines a Fourth Major Subgroup of T4-Like Phages in *Escherichia coli*," J. Bacteriol., vol. 189, No. 22, pp. 8206-8214, Nov. 2007.

Niu et al., "Host range and lytic capability of four bacteriophages against bovine and clinical human isolates of Shiga toxin-producing *Escherichia coli* O157:H7," Journal of Applied Microbiology, vol. 107, pp. 646-656, 2009.

Weiss et al., "In vivo replication of T4 and T7 bacteriophages in germ-free mice colonized with *Escherichia coli*," Virology, vol. 393, pp. 16-23, Aug. 2009.

Maura et al., "On the interactions between virulent bacteriophages and bacteria in the gut," Bacteriophage, vol. 2, No. 4, pp. 229-233, Oct./Nov./Dec. 2012.

Denou et al., "T4 phages against *Escherichia coli* diarrhea: Potential and problems," Virology, vol. 388, pp. 21-30, Apr. 2009.

Strober, "Adherent-invasive *E. coli* in Crohn disease: bacterial "agent provocateur"," The Journal of Clinical Investigation, vol. 121, pp. 841-844, 2011.

Conte et al., "Adherent-invasive *Escherichia coli* (AIEC) in pediatric Crohn's disease patients: phenotypic and genetic pathogenic features," BMC Research Notes, vol. 7, No. 748, pp. 1-12, Oct. 2014.

Baumgart et al., "Culture independent analysis of ileal mucosa reveals a selective increase in invasive *Escherichia coli* of novel phylogeny relative to depletion of Clostridiales in Crohn's disease involving the ileum," The ISME Journal, vol. 1, pp. 403-418, Jul. 2007.

Office Action dated May 28, 2019 in Japanese Application No. 2016-511060.

Galtier et al., "Bacteriophages Targeting Adherent Invasive *Escherichia Coli* Strains as a Promising New Treatment for Crohn's Disease," Journal of Crohn's and Colitis, 11(7):840-847 (Jan. 2017).

* cited by examiner

BACTERIOPHAGE THERAPY

CROSS-REFERENCE TO RELATED APPLICATIONS

The present application is a divisional of U.S. patent application Ser. No. 14/787,581, filed Oct. 28, 2015, which is the U.S. National Stage of International Application No. PCT/EP2014/058840, filed Apr. 30, 2014, and claims priority to European Patent Application No. 13305568.1, filed Apr. 30, 2013.

FIELD OF THE INVENTION

The present invention lies in the field of bacteriophage therapy for use in the treatment of inflammatory bowel diseases.

BACKGROUND

Bacteriophages are viruses that infect bacteria by specific interaction.

Crohn's disease (CD), also known as regional enteritis, is an inflammatory disease of the intestines that may affect any part of the gastrointestinal tract from mouth to anus, causing a wide variety of symptoms. It primarily causes abdominal pain, diarrhea, vomiting, or weight loss, but may also cause complications outside the gastrointestinal tract such as skin rashes, arthritis, inflammation of the eye, tiredness, and lack of concentration.

Although the exact cause of CD is still unknown, a combination of environmental factors and genetic predisposition seems to cause the disease. CD is thought to be an autoimmune disease, in which the body's immune system attacks the gastrointestinal tract, causing inflammation; it is classified as a type of inflammatory bowel disease (IBD).

In patients with CD, abnormal expression of carcinoembryonic antigen-related cell adhesion molecule 6 (CEACAM6) is observed at the apical surface of the ileal epithelium and CD ileal lesions are colonized by pathogenic adherent-invasive *Escherichia coli* (AIEC).

There is no known pharmaceutical or surgical cure for Crohn's disease. In particular, neither IBD in general nor CD in particular can be treated with antibiotics (aiming at combatting pathogenic *E. coli*). Treatment options are restricted to controlling symptoms, maintaining remission, and preventing relapse.

SUMMARY OF THE INVENTION

The subject invention provides a pharmaceutical composition comprising: (i) at least one bacteriophage strain capable of producing a lytic infection in an adherent-invasive *Escherichia coli* strain; and (ii) a pharmaceutically acceptable carrier; for the treatment of inflammatory bowel disease (IBD).

The subject invention further provides a method of treating inflammatory bowel disease comprising administering to a subject in need thereof at least one bacteriophage strain capable of producing a lytic infection in an adherent-invasive *Escherichia coli* strain thereby treating the subject.

The subject invention further provides a bacteriophage strain P1 deposited with the French National Collection of Microorganisms at the Institut Pasteur under Accession Number CNCM I-4694 or a variant thereof, wherein the variant has the same lytic activity, preferably the same lytic activity and the same phenotypic characteristics as said bacteriophage strain.

The subject invention further provides a bacteriophage strain P2 deposited with the French National Collection of Microorganisms at the Institut Pasteur under Accession Number CNCM I-4695 or a variant thereof, wherein the variant has the same lytic activity, preferably the same lytic activity and the same phenotypic characteristics as said bacteriophage strain.

The subject invention further provides a bacteriophage strain P3 deposited with the French National Collection of Microorganisms at the Institut Pasteur under Accession Number CNCM I-4696 or a variant thereof, wherein the variant has the same lytic activity, preferably the same lytic activity and the same phenotypic characteristics as said bacteriophage strain.

The subject invention further provides a bacteriophage strain P4 deposited with the French National Collection of Microorganisms at the Institut Pasteur under Accession Number CNCM I-4697 or a variant thereof, wherein the variant has the same lytic activity, preferably the same lytic activity and the same phenotypic characteristics as said bacteriophage strain.

The subject invention further provides a bacteriophage strain P5 deposited with the French National Collection of Microorganisms at the Institut Pasteur under Accession Number CNCM I-4698 or a variant thereof, wherein the variant has the same lytic activity, preferably the same lytic activity and the same phenotypic characteristics as said bacteriophage strain.

The subject invention further provides a bacteriophage strain P6 deposited with the French National Collection of Microorganisms at the Institut Pasteur under Accession Number CNCM I-4699 or a variant thereof, wherein the variant has the same lytic activity, preferably the same lytic activity and the same phenotypic characteristics as said bacteriophage strain.

The subject invention further provides a bacteriophage strain P8 deposited with the French National Collection of Microorganisms at the Institut Pasteur under Accession Number CNCM I-4700 or a variant thereof, wherein the variant has the same lytic activity, preferably the same lytic activity and the same phenotypic characteristics as said bacteriophage strain.

The subject invention also makes use of bacteriophage strain CLB_P2 deposited with the French National Collection of Microorganisms at the Institut Pasteur under Accession Number CNCM I-4675 or a variant thereof, wherein the variant has the same lytic activity, preferably the same lytic activity and the same phenotypic characteristics as said bacteriophage strain.

For the purpose of the present invention, a variant of a bacteriophage strain is regarded as having the same lytic activity as said bacteriophage strain if it performs at least "+" against at least one of the AIEC strains LF82, 07081, 07082, 07076 and 06075 in the "In vitro assay of the infectivity of bacteriophages in AIEC strains" described in Example 3 below. In a preferred embodiment, a variant is regarded as having the same lytic activity if it performs at least "+" against all five AIEC strains LF 82, LF 06075, LF 07076, LF 07081 and LF 07082 (AIEC strains LF 06075, LF 07076, LF 07081 and LF 07082 are also abbreviated herein as 06075, 07076, 07081 and 07082, respectively). These AIEC strains have been deposited by Université Lille 2-Droit et Santé, 42 Rue Paul Duez, 59000 Lille (France) with the French National Collection at Institut Pasteur under Accession Numbers CNCM I-4712 (LF 82), CNCM I-4713 (LF 06075), CNCM I-4714 (LF 07076), CNCM I-4715 (LF 07081) and CNCM I-4716 (LF 07082).

For the purpose of the present invention, a variant of one of the bacteriophage strains P1 to P6, P8 and CLB_P2 is regarded as having the same phenotypic characteristics as said bacteriophage strain if it has at least 80% sequence identity on at least 70% of length, preferably at least 90% sequence identity on at least 80% of length and more preferably complete sequence identity on at least 90% of length (as determined by the BLAST algorithm) with the major capsid protein of bacteriophage wV8 (for variants of P1 to P6) or bacteriophage RB69 (for variants of P8) or bacteriophage JS98 (for variants of CLB_P2), as described below in the section "Identification of Major Capsid Proteins".

In a preferred embodiment, a variant of a bacteriophage has the same lytic activity as the bacteriophage. In another embodiment, a variant of a bacteriophage has the same lytic activity and the same phenotypic characteristics as the bacteriophage.

DETAILED DESCRIPTION OF THE INVENTION

The subject invention provides a pharmaceutical composition comprising: (i) at least one bacteriophage strain capable of producing a lytic infection in an adherent-invasive *Escherichia coli* strain; and (ii) a pharmaceutically acceptable carrier; for the treatment of inflammatory bowel disease.

The subject invention further provides for a method of treating inflammatory bowel disease comprising administering to a subject in need thereof at least one bacteriophage strain capable of producing a lytic infection in an adherent-invasive *Escherichia coli* strain thereby treating the subject.

An "adherent-invasive *Escherichia coli* (AIEC) strain" as used herein should be understood as referring to an *E. coli* strain having a mean invasion potential of equal to or higher than 0.1% in a cell culture of the intestinal cell line I-407. In other words, an AIEC strain has the ability to invade an intestinal cell culture of I-407 with an invasion index equal or superior to 0.1% of the original inoculum (taken as 100%), when tested in accordance with the invasion assay described below in the section "Invasion Assay" (see also Darfeuille-Michaud et al. (2004), *Gastroenterology* 127: 412-421).

Non-limiting examples of AIEC strains are LF82, LF82SK (deposited by Université d'Auvergne, 49 Boulevard François Mitterand, 63001 Clermont-Ferrand (France) with the French National Collection at Institut Pasteur under Accession Number CNCM I-4723), those listed in Table 1 herein below and those listed in the following itemization (cf. Darfeuille-Michaud et al. (2004), *Gastroenterology* 127: 412-421, especially page 417, Table 2): LF31, LF71, LF123, LF138, LF9, LF15, LF28, LF50, LF65, LF119, LF128, LF130, LF73, LF100, LF110, LF134, LF105, LF49-2, LB11, and LF45-2. In one embodiment, the adherent-invasive *Escherichia coli* strain is LF82, 07081, 07082, 07076 or 06075, in particular LF82.

In one embodiment, the adherent-invasive *Escherichia coli* strain is present in the colon of the subject. In another embodiment, the adherent-invasive *Escherichia coli* strain is present in the ileum of the subject. In yet another embodiment, the adherent-invasive *Escherichia coli* strain is present in one or more intestinal parts (small and/or large) of the subject.

In one embodiment, the at least one bacteriophage strain is P1 deposited with the French National Collection of Microorganisms at the Institut Pasteur under Accession Number CNCM I-4694 or a variant thereof, wherein the variant has the same lytic activity, preferably the same lytic activity and the same phenotypic characteristics as said bacteriophage strain.

In one embodiment, the at least one bacteriophage strain is P2 deposited with the French National Collection of Microorganisms at the Institut Pasteur under Accession Number CNCM I-4695 or a variant thereof, wherein the variant has the same lytic activity, preferably the same lytic activity and the same phenotypic characteristics as said bacteriophage strain.

In one embodiment, the at least one bacteriophage strain is P3 deposited with the French National Collection of Microorganisms at the Institut Pasteur under Accession Number CNCM I-4696 or a variant thereof, wherein the variant has the same lytic activity, preferably the same lytic activity and the same phenotypic characteristics as said bacteriophage strain.

In one embodiment, the at least one bacteriophage strain is P4 deposited with the French National Collection of Microorganisms at the Institut Pasteur under Accession Number CNCM I-4697 or a variant thereof, wherein the variant has the same lytic activity, preferably the same lytic activity and the same phenotypic characteristics as said bacteriophage strain.

In one embodiment, the at least one bacteriophage strain is P5 deposited with the French National Collection of Microorganisms at the Institut Pasteur under Accession Number CNCM I-4698 or a variant thereof, wherein the variant has the same lytic activity, preferably the same lytic activity and the same phenotypic characteristics as said bacteriophage strain.

In one embodiment, the at least one bacteriophage strain is P6 deposited with the French National Collection of Microorganisms at the Institut Pasteur under Accession Number CNCM I-4699 or a variant thereof, wherein the variant has the same lytic activity, preferably the same lytic activity and the same phenotypic characteristics as said bacteriophage strain.

In one embodiment, the at least one bacteriophage strain is P8 deposited with the French National Collection of Microorganisms at the Institut Pasteur under Accession Number CNCM I-4700 or a variant thereof, wherein the variant has the same lytic activity, preferably the same lytic activity and the same phenotypic characteristics as said bacteriophage strain.

In one embodiment, the at least one bacteriophage strain is CLB_P2 deposited with the French National Collection of Microorganisms at the Institut Pasteur under Accession Number CNCM I-4675 or a variant thereof, wherein the variant has the same lytic activity, preferably the same lytic activity and the same phenotypic characteristics as said bacteriophage strain.

In one aspect, it is envisaged that the pharmaceutical composition comprises more than one bacteriophage strain, also named "a bacteriophage cocktail". The bacteriophage cocktail of the present invention comprises any combination of two or more of P1, P2, P3, P4, P5, P6, P8 and CLB_P2 and variants thereof having the same lytic activity, preferably the same lytic activity and the same phenotypic characteristics. Preferably, the bacteriophages in a bacteriophage cocktail intended for treatment of a specific subject or group of subjects will be selected on the basis of the AIEC strain or AIEC strains identified and selected for combatting.

Non-limiting examples of inflammatory bowel diseases are Crohn's disease (CD), ulcerative colitis (UC), chronic inflammatory bowel disease (chronic IBD) such as but not limited to microscopic colitis, celiac disease and vasculitis. In one embodiment, the IBD is CD or UC. In another embodiment, the inflammatory bowel disease is recurrence of ileal lesions after surgery (such as surgery for the removal of at least a part of the small intestine in CD patients). The recurrence can be measured by the Rutgeerts score.

In one embodiment, the IBD is not caused by a bacterial infection. This embodiment is based on the observation that IBD is an autoimmune disease which is not generally considered a bacterial disease. Instead, a bacterial infection may be concomitant to IBD, but is not necessarily the causative agent. This observation adds to the surprising finding of the present invention, namely applying bacteriophage therapy for the treatment of a disease which is not caused by bacteria.

For that reason, there can be—as an example—AIEC strains in family members of subjects suffering from an IBD, although these family members do not suffer from this disease. Likewise, AIEC strains can also be found in subjects neither suffering from IBD nor being related to subjects suffering from IBD, as can also be seen from Table 1 below.

"Treating" as used herein should be understood to encompass a decrease in one or more symptoms characteristic of the disease; a decrease in the rate of progression of the disease; recovery from the disease, cure from the disease, maintenance of remission and prophylaxis such as prevention of relapse.

A "subject" as used herein can be a male or a female subject. A subject can be a human being or any other mammal.

The dose and regimen of administration of a pharmaceutical composition of the invention will necessarily be dependent upon the therapeutic effect to be achieved (e.g. treatment of IBD) and may vary with the particular bacteriophage strains in the composition, the route of administration, and the age and condition of the individual subject to whom the medicament is to be administered.

A dosage for humans is likely to contain a dose of bacteriophage between $10^4$ and $10^{11}$ plaque forming units (pfu). The desired dose may be presented as one dose per day or as multiple sub-doses administered at appropriate intervals.

In the context of the present invention the term "pharmaceutically acceptable carrier" relates to pharmaceutically-acceptable, non-toxic carriers, fillers or diluents, which are defined as vehicles commonly used to formulate pharmaceutical compositions for animal or human administration.

The pharmaceutical compositions of the present invention may further comprise pharmaceutically acceptable auxiliary agents, and optionally other therapeutic agents. Auxiliary agents, also named accessory ingredients, encompass those conventional in the art such as, but not limited to matrix-forming agents, thickeners, binders, lubricants, pH adjusting agents, protecting agents, viscosity enhancers, wicking agents, disintegrants, including non-effervescent and effervescent disintegrants, surfactants, anti-oxidants, wetting agents, colorants, flavoring agents, taste-masking agents, sweeteners, preservatives and so forth. In addition to being pharmaceutically acceptable, the auxiliary agents must be "acceptable" in the sense that they are compatible with the other ingredients of the composition, including the bacteriophage.

Pharmaceutical compositions and routes of administration include those suitable for or via oral (including buccal, sublingual and intraorbital), rectal, nasal, topical (including transdermal), ocular, otic, vaginal, bronchial, pulmonary or parenteral (including subcutaneous, intramuscular, intravenous, intradermal, intraperitoneal, intrapleural, intravesicular and intrathecal) administration or administration via an implant. The pharmaceutical composition or route of administration may be adapted to provide a targeted effect of bacteriophage strain of the invention. In a specific embodiment, a pharmaceutical composition of the invention is administered orally. The compositions may be prepared by any method well known in the art of pharmacy. Such methods include the step of bringing in association a bacteriophage strain of the invention with a pharmaceutically acceptable carrier and optionally one or more auxiliary agents.

Pharmaceutical compositions suitable for oral administration may be presented as discrete dosage units (dosage forms) such as pills, tablets, dragees or capsules, or as a powder or granules, or as a solution or suspension. The pharmaceutical composition may also be presented as a bolus or paste. The compositions can further be processed into a suppository or enema for rectal administration.

For parenteral administration, suitable compositions include aqueous and non-aqueous sterile injections. The compositions may be presented in unit-dose or multi-dose containers, for example sealed vials and ampoules, and may be stored in a freeze-dried (lyophilized) condition requiring only the addition of sterile liquid carrier, for example water, prior to use.

For transdermal administration, e.g., gels, patches or sprays can be contemplated.

Compositions or formulations suitable for pulmonary administration, e.g., by nasal inhalation, include fine dusts or mists which may be generated by means of metered dose pressurized aerosols, nebulizers or insufflators.

The invention further includes a kit comprising a pharmaceutical composition of the invention and instructions for the use of the composition for a use as hereinbefore described, optionally together with packaging material.

The subject invention further provides a bacteriophage strain P1 deposited with the French National Collection of Microorganisms at the Institut Pasteur under Accession Number CNCM I-4694 or a variant thereof, wherein the variant has the same lytic activity, preferably the same lytic activity and the same phenotypic characteristics as said bacteriophage strain.

The subject invention further provides a bacteriophage strain P2 deposited with the French National Collection of Microorganisms at the Institut Pasteur under Accession Number CNCM I-4695 or a variant thereof, wherein the variant has the same lytic activity, preferably the same lytic activity and the same phenotypic characteristics as said bacteriophage strain.

The subject invention further provides a bacteriophage strain P3 deposited with the French National Collection of Microorganisms at the Institut Pasteur under Accession Number CNCM I-4696 or a variant thereof, wherein the variant has the same lytic activity, preferably the same lytic activity and the same phenotypic characteristics as said bacteriophage strain.

The subject invention further provides a bacteriophage strain P4 deposited with the French National Collection of Microorganisms at the Institut Pasteur under Accession Number CNCM I-4697 or a variant thereof, wherein the variant has the same lytic activity, preferably the same lytic activity and the same phenotypic characteristics as said bacteriophage strain.

The subject invention further provides a bacteriophage strain P5 deposited with the French National Collection of Microorganisms at the Institut Pasteur under Accession Number CNCM I-4698 or a variant thereof, wherein the variant has the same lytic activity, preferably the same lytic activity and the same phenotypic characteristics as said bacteriophage strain.

The subject invention further provides a bacteriophage strain P6 deposited with the French National Collection of Microorganisms at the Institut Pasteur under Accession Number CNCM I-4699 or a variant thereof, wherein the variant has the same lytic activity, preferably the same lytic activity and the same phenotypic characteristics as said bacteriophage strain.

The subject invention further provides a bacteriophage strain P8 deposited with the French National Collection of Microorganisms at the Institut Pasteur under Accession Number CNCM I-4700 or a variant thereof, wherein the variant has the same lytic activity, preferably the same lytic activity and the same phenotypic characteristics as said bacteriophage strain.

EXAMPLES

The invention is further described in the following examples, which are not in any way intended to limit the scope of the invention as claimed.

Methods

Invasion Assay

The Intestine-407 (I-407) cell line derived from human embryonic jejunum and ileum was used as a model of undifferentiated intestinal epithelial cells. It was purchased from Flow Laboratories (Flow Laboratories Inc., Mc Lean, VA).

Intestine-407 cells were seeded in 24-well tissue culture plates (Polylabo, Strasbourg, France) at a density of 4,105 cells/well and incubated for 20 hours. The cell monolayers were washed twice with PBS (pH 7.2). Bacterial invasion of epithelial cells was measured using the gentamicin protection assay (Falkow et al. (1987), Rev. Infect. Dis. 9 (Suppl. 5):5450-455). Each monolayer was inoculated in 1 mL of the cell culture medium lacking antibiotics with a multiplicity of infection of 10 bacteria per epithelial cell. After a 3-hour incubation period at 37° C. with 5% $CO_2$, the monolayers were washed 3 times with PBS. Fresh cell culture medium containing 100 µg/mL of gentamicin (Sigma, St. Louis, MO) was added for 1 hour to kill extracellular bacteria before lysis of the monolayers with 1% Triton X-100 (Sigma) in deionized water. This concentration of Triton X-100 had no effect on bacterial viability for at least 30 minutes. The samples were diluted and plated onto Mueller-Hinton agar plates to determine the number of colony-forming units. All results of *E. coli* invasive ability with Intestine-407 cell line were expressed as the percentage of intracellular bacteria compared with the initial inoculum, taken as 100%. All of the assays were performed at least 3 times in separate experiments.

Identification of Major Capsid Proteins

Virion proteins were obtained by boiling 60 µl of a suspension of $10^{11}$ pfu/ml of each bacteriophage for 10 min. 20 µl of the suspension were run on a precast 4-12% polyacrylamide gel. The gel was stained with Coomassie blue and the major bands were excised, subjected to trypsin digestion and analyzed by mass spectrometry at the Institut Pasteur microsequencing facility.

The peptide masses obtained were compared with the information in protein databases, allowing the identification of the closest known protein, i.e. wV8 for P1 to P6 and RB69 for P8 and JS98 for CLB_P2 (see A. Villegas et al, Virology Journal 2009, 6:41 for characterization of wV8 and S. Zuber et al., Journal of Bacteriology 2007, 189:22, 8206 for characterization of RB69 and JS 98).

Alignment of the major capsid protein of bacteriophage wV8 with peptides obtained from mass spectrometry of the major capsid proteins of bacteriophages P1 to P6:

```
wV8:  MLTNSEKSRFFLADLTGEVQSIPNTYGYISNLGLFRSAPITQTTFLMDLTDWDVSLLDAVDRDSRKAE
P1:             FFLADLTGEVQSIPNTYGYISNLGLFR (SEQ ID NO: 2)
P2:   SRFFLADLTGEVQSIPNTYGYISNLGLFRSAPITQTTFLMDLTDWDVSLLDAVDR (SEQ ID NO: 3)
P3:
P4:
P5:
P6:

wV8:  TSAPERVRQISFPMMYFKEVESITPDEIQGVRQPGTANELTTEAVVRAKKLMKIRTKFDITREFLFMQ
P1:              QISFPMMYFKEVESITPDEIQGVRQPGTANELTTEAVVR        TKFDITREFLFMQ
                 (SEQ ID NO: 4)                                (SEQ ID NO: 5)
P2:              QISFPMMYFKEVESITPDEIQGVRQPGTANELTTEAVVR        TKFDITREFLFMQ
                 (SEQ ID NO: 4)                                (SEQ ID NO: 5)
P3:              QISFPMMYFKEVESITPDEIQGVRQPGTANELTTEAVVR        TKFDITREFLFMQ
                 (SEQ ID NO: 4)                                (SEQ ID NO: 5)
P4:              QISFPMMYFKEVESITPDEIQGVRQPGTANELTTEAVVR        TKFDITREFLFMQ
                 (SEQ ID NO: 4)                                (SEQ ID NO: 5)
P5:              QISFPMMYFKEVESITPDEIQGVRQPGTANELTTEAVVR        TKFDITREFLFMQ
                 (SEQ ID NO: 4)                                (SEQ ID NO: 5)
P6:              QISFPMMYFKEVESITPDEIQGVRQPGTANELTTEAVVR        TKFDITREFLFMQ
                 (SEQ ID NO: 4)                                (SEQ ID NO: 5)

wV8:  ALKGKVVDARGTLYADLYKQFDVEKKTVYFDLDNPNADIDAAIEELRMHMEDEAKTGTVINGEEIHVV
P1:   ALK        GTLYADLYK       KTVYFDLDNPNADIDASIEELR         TGTVINGEEIHVV
                 (SEQ ID NO: 6)  (SEQ ID NO: 8)                 (SEQ ID NO: 11)
P2:   ALK        GTLYADLYK                                      TGTVINGEEIHVV
                 (SEQ ID NO: 6)                                 (SEQ ID NO: 12)
P3:   ALK        GTLYADLYK       TVYFDLDNPNADIDASIEELR          TGTVINGEEIHVV
                 (SEQ ID NO: 6)  (SEQ ID NO: 9)                 (SEQ ID NO: 11)
```

```
                                           -continued
P4: ALK         GTLYADLYK                                     TGTVINGEEIHVV
                (SEQ ID NO: 6)                                (SEQ ID NO: 11)
P5: ALK         GTLYADLYK         TIYFDLDNPNADIDASIEELR       TGTVINGEEIHVV
                (SEQ ID NO: 6)    (SEQ ID NO: 10)             (SEQ ID NO: 11)
P6: ALK         GTLYADLYKQFDVEK   TIYFDLDNPNADIDASIEELR       TGTVINGEEIHVV
                (SEQ ID NO: 7)    (SEQ ID NO: 10)             (SEQ ID NO: 11)

wV8: VDRLFFSKLVKHPKIRDAYLAQQTPLAWQQITGSLRTGGTDGVQAHMNTFYYGGVKFVQYNGKFKDKR
P1:  VDR          IRDAYLAQQTPLAWQQITGSLR                     FVQYNGK
                  (SEQ ID NO: 13)                            (SEQ ID NO: 18)
P2:  VDRLFFSK     IRDAYLAQQTPLAWQQITGSLRTGGTDGVQAHMNTFYYGGVKFVQYNGK
                  (SEQ ID NO: 14)
P3:  VDR          DAYLAQQTPLAWQQITGSLR                       FVQYNGK
                  (SEQ ID NO: 15)                            (SEQ ID NO: 18)
P4:  VDR          DAYLAQQTPLAWQQITGSLR                       FVQYNGK
                  (SEQ ID NO: 15)                            (SEQ ID NO: 18)
P5:  VDR          DAYLAQQTPLAWQQITGSLRTGGADGVQAHMNTFYYGGVKFVQYNGK
                  (SEQ ID NO: 16)
P6:               DAYLAQQTPLAWQQITGSLRTGGADGVQAHMNTFYYGGVK
                  (SEQ ID NO: 17)

wV8: GKVHTLVSIDSVAATVGVGHAFPNVSMLGEANNIFEVAYGPCPKMGYANTLGQELYVFEYEKDRDEGI
P1:                                          MGYANTLGQELYVFEYEKDR
                                             (SEQ ID NO: 19)
P2:                                          MGYANTLGQELYVFEYEKDR
                                             (SEQ ID NO: 19)
P3:
P4:
P5:
P6:

wV8: DFEAHSYMLPYCTRPQLLVDVRSDAKPD (SEQ ID NO: 1)
P1:                PQLLVDVR (SEQ ID NO: 20)
P2:                PQLLVDVR (SEQ ID NO: 20)
P3:                PQLLVDVR (SEQ ID NO: 20)
P4:                PQLLVDVR (SEQ ID NO: 20)
P5:                PQLLVDVR (SEQ ID NO: 20)
P6:                PQLLVDVR (SEQ ID NO: 20)
```

Alignment of the major capsid protein of bacteriophage RB69 with peptides obtained from mass spectrometry of the major capsid protein of bacteriophage P8:

```
RB69: MTTIKTKAQLVDKWKELLEGEGLPEIANSKQAIIAKIFENQEKDFEVSPEYKDEKIAQAFGSFLTEAE
P8:

RB69: IGGDHGYNAQNIAAGQTSGAVTQIGPAVMGMVRRAIPNLIAFDICGVQPMNSPTGQVFALRAVYGKDP
P8:

RB69: IAAGAKEAFHPMYAPDAMFSGQGAAKKFPALAASTQTKVGDIYTHFFQETGTVYLQASAQVTISSSAD
P8:            EAFHPMYAPDAMFSGQGAAK
               (SEQ ID NO: 22)

RB69: DAAKLDAEIIKQMEAGALVEIAEGMATSIAELQEGFNGSTDNPWNEMGFRIDKQVIEAKSRQLKAAYS
P8:                                                                    AAYS

RB69: IELAQDLRAVHGMDADAELSGILATEIMLEINREVVDWINYSAQVGKSGMTNIVGSKAGVFDFQDPID
P8:   IELAQDLR                      EVVDWINYSAQVGK       AGVFDFQDPID
      (SEQ ID NO: 23)               (SEQ ID NO: 24)     (SEQ ID NO: 25)

RB69: IRGARWAGESFKALLFQIDKEAVEIARQTGRGEGNFIIASRNVVNVLASVDTGISYAAQGLASGFNTD
P8:   IR   WAGESFK            QTGRGEGNFIIASR
           (SEQ ID NO: 26)    (SEQ ID NO: 27)

RB69: TTKSVFAGVLGGKYRVYIDQYAKDYFTVGYKGANEMDAGIYYAPYVALTPLRGSDPKNFQPVMGFKT
P8:      SVFAGVLGGKYRVYIDQYAKDYFTVGYKGANEMDAGIYYAPYVALTPLR   NFQPVMGFKT
         (SEQ ID NO: 28)                                    (SEQ ID NO: 29)

RB69: RYGIGVNPFAESSLQAPGARIQSGMPSILNSLGKNAYFRRVYVKGI (SEQ ID NO: 21)
P8:   RYGIGVNPFAESSLQAPGARIQSGMPSILNSLGK
```

Alignment of the major capsid protein of bacteriophage JS98 with peptides obtained from mass spectrometry of the major capsid protein of bacteriophage CLB_P2.

```
JS98:    MKKNALVQKWSALLENEALPEIVGASKQAIIAKIFENQEQDILTAPEYRDEKISEAFGSFLTEAEI
CLB_P2:

JS98:    GGDHGYDATNIAAGQTSGAVTQIGPAVMGMVRRAIPHLIAFDICGVQPLNNPTGQVFALRAVYGKD
CLB_P2:                                                                AVYGKD
                                                                    (SEQ ID NO: 35)

JS98:    PIAAGAKEAFHPMYAPNAMFSGQGAAETFEALAASKVLEVGKIYSHFFEATGSAHFQAVEAVTVDA
CLB_P2:  PIAAGAK

JS98:    GATDAAKLDAAVTALVEAGQLAEIAEGMATSIAELQEGFNGSTDNPWNEMGFRIDKQVIEAKSRQL
CLB_P2:

JS98:    KASYSIELAQDLRAVHGMDADAELSGILATEIMLEINREVIDWINYSAQVGKSGMTNTVGAKAGVF
CLB_P2:  ASYSIELAQDLR                       EVIDWINYSAQVGK            AGVF
         (SEQ ID NO: 36)                    (SEQ ID NO: 37) (SEQ ID NO: 38)

JS98:    DFQDPIDIRGARWAGESFKALLFQIDKEAAEIARQTGRGAGNFIIASRNVVNVLAAVDTSVSYAAQ
CLB_P2:  DFQDPIDIR    WAGESFKALLFQIDKEAAEIAR    GAGNFIIASR
                 (SEQ ID NO: 39)              (SEQ ID NO: 40)

JS98:    GLGQGFNVDTTKAVFAGVLGGKYRVYIDQYARSDYFTIGYKGSNEMDAGIYYAPYVALTPLRGSDP
CLB_P2:                 AVFAGVLGGKYRVYIDQYAR       GSNEMDAGIYYAPYVALTPLR
                    (SEQ ID NO: 41)              (SEQ ID NO: 42)

JS98:    KNFQPVMGFKTRYGIGINPFADPAAQAPTKRIQNGMPDIVNSLGLNGYFRRVYVKGI (SEQ ID NO: 34)
CLB_P2:  NFQPVMGFKTRYGIGINPFADPAAQAPTKRIQNGMPDIVNSLGLNGYFR
             (SEQ ID NO: 43)
```

Example 1

Isolation of AIEC Strains

One hundred and sixty-six (166) adherent-invasive *Escherichia coli* (*E. coli*) strains, including *E. coli* strain LF82 (Table 1), were isolated as follows: The AIEC strains were isolated from fresh feces of CD patients, their family members and control subjects. The feces were diluted in tenfold dilutions up to −9. Each dilution was plated on different media. After incubation, colonies were sub-cultured, identified and the strains were tested for invasion capacity.

In detail, immediately after emission, fresh feces were introduced in a sterile container. The atmosphere was rendered anaerobic by addition of a moistened Anaerocult®. Samples were treated the day of sampling. About 1 g of feces were introduced in 9 mL of cysteinated ¼ strength Ringer solution in pre-weighed tubes; they were reweighed after introduction of the sample to determine its exact weight (first tenfold dilution). Eight further tenfold dilutions were made and 0.1 mL of each dilution was plated on different non-selective and selective media incubated in appropriated conditions: Columbia blood agar (CS) and CSH agar incubated for one week under anaerobic conditions, MRS medium incubated for 48 h in an atmosphere enriched in $CO_2$, McConkey and Cetrimide agar incubated for 48 h in air. All incubations were done at 37° C. After incubation, colonies were counted, subcultured and identified by established phenotypic criteria.

A control subject was selected vis-á-vis a CD patient so that the control subject was of the same sex and age as the CD patient and had a similar family size as the CD patient (to take microflora variation within a family into consideration).

The protocol was approved by the local ethical committee in 2000. The patients were followed by the EPIMAD register, which is organized under an agreement between the Institut National de la Santé et de la Recherche Médicale (INSERM) and the Institut National de Veille Sanitaire (InVS) and is also supported by the Francois Aupetit Association, Lion's Club of Northwestern France, Ferring Laboratories, the Société Nationale Française de Gastroentérologie and Lille University Hospital.

TABLE 1

| | | AIEC strains | | | | |
|---|---|---|---|---|---|---|
| Number | Reference | Invasion I-407 Mean (%) | Invasion I-407 SEM (%) | Culture Medium [1] | Dilution | Level of *E. coli* (log UFC/g) [2] | Total Count (logUFC/g) [3] |
| | LF82 | 1.29 | 0.8 | McC | −4 | 5.7 | 5.9 |
| | | AIEC isolated from CD patient | | | | | |
| 06259 | C4-1 | 2.050 | 0.500 | McC | −5 | 5.87 | 10.52 |
| 06254 | C34-12 | 2.163 | 0.738 | Cet | −2 | 2.91 | 10.14 |
| 06256 | C34-2 | 0.550 | 0.170 | McC | −7 | 7.91 | 10.14 |
| 06072 | C39-1 | 0.2075 | 0.147 | McC | −6 | 7.02 | 9.93 |
| 06073 | C39-2 | 0.1374 | 0.097 | McC | −6 | 7.02 | 9.93 |
| 06075 | C39-4 | 0.2334 | 0.165 | McC | −5 | 6.02 | 9.93 |
| 06076 | C39-7 | 0.5900 | 0.417 | Cet | −2 | 3.02 | 9.93 |
| 06087 | C42-1 | 0.1095 | 0.055 | McC | −5 | 5.82 | 9.58 |
| 06088 | C42-2 | 0.1954 | 0.098 | McC | −5 | 5.82 | 9.58 |
| 06089 | C42-3 | 0.1930 | 0.097 | Cet | −3 | 3.82 | 9.58 |
| 06398 | C76-10 | 0.131 | 0.036 | CS ana | −5 | 6.09 | 9.99 |

TABLE 1-continued

| | | AIEC strains | | | | | |
|---|---|---|---|---|---|---|---|
| Number | Reference | Invasion I-407 Mean (%) | Invasion I-407 SEM (%) | Culture Medium [1] | Dilution | Level of E. coli (log UFC/g) [2] | Total Count (logUFC/g) [3] |
| 06011 | C84-2 | 0.2580 | 0.129 | McC | −6 | 6.96 | 9.23 |
| 06023 | C97-1 | 0.1173 | 0.068 | McC | −7 | 8.14 | 10.03 |
| 06024 | C97-2 | 0.1303 | 0.075 | McC | −6 | 7.14 | 10.03 |
| 06026 | C98-1 | 0.1439 | 0.072 | McC | −6 | 7.2 | 9.34 |
| 06027 | C98-2 | 0.1122 | 0.065 | McC | −6 | 7.2 | 9.34 |
| 06028 | C98-4 | 0.2310 | 0.133 | Cet | −2 | 3.20 | 9.34 |
| 06029 | C99-1 | 1.0657 | 0.615 | McC | −6 | 6.99 | 10.17 |
| 06030 | C99-2 | 0.1613 | 0.081 | McC | −6 | 6.99 | 10.17 |
| 06031 | C99-3 | 0.2330 | 0.135 | McC | −5 | 5.99 | 10.17 |
| 06033 | C99-9 | 0.4667 | 0.269 | Cet | −2 | 2.99 | 10.17 |
| 06150 | C187-13 | 0.6675 | 0.472 | CS ana | −7 | 7.93 | 9.97 |
| 06151 | C187-14 | 1.0350 | 0.732 | CS ana | −7 | 7.93 | 9.97 |
| 06152 | C187-15 | 0.4375 | 0.253 | CS ana | −7 | 7.93 | 9.97 |
| 06166 | C190-1 | 0.2251 | 0.130 | McC | −8 | 9.28 | 10.98 |
| 06167 | C190-2 | 0.1247 | 0.072 | McC | −8 | 9.28 | 10.98 |
| 06168 | C190-3 | 0.1688 | 0.097 | McC | −7 | 8.28 | 10.98 |
| 06169 | C190-4 | 0.1373 | 0.079 | McC | −6 | 7.28 | 10.98 |
| 06170 | C190-6 | 0.7065 | 0.408 | Cet | −3 | 4.28 | 10.98 |
| 06171 | C190-8 | 0.5827 | 0.336 | Cet | −2 | 3.28 | 10.98 |
| 06172 | C190-7 | 0.5385 | 0.311 | Cet | −2 | 3.28 | 10.98 |
| 06173 | C190-12 | 0.5182 | 0.299 | CS ana | −9 | 10.28 | 10.98 |
| 06280 | C203-7 | 0.185 | 0.087 | Cet | −3 | 3.96 | 9.94 |
| 06281 | C203-9 | 0.393 | 0.023 | Cet | −2 | 2.96 | 9.94 |
| 06283 | C204-4 | 0.253 | 0.092 | McC | −6 | 7.00 | 9.78 |
| 06271 | C205-2 | 0.153 | 0.052 | McC | −6 | 6.93 | 9.97 |
| 06278 | C205-9 | 0.160 | 0.005 | Cet | −2 | 2.93 | 9.97 |
| 06351 | C215-8 | 0.548 | 0.397 | Cet | −5 | 5.93 | 9.91 |
| 06352 | C215-9 | 0.262 | 0.143 | Cet | −5 | 5.93 | 9.91 |
| 06353 | C215-12 | 1.960 | 1.340 | Cet | −3 | 3.93 | 9.91 |
| 06354 | C215-13 | 1.339 | 1.281 | Cet | −3 | 3.93 | 9.91 |
| 06356 | C215-10 | 2.260 | 1.540 | Cet | −3 | 3.93 | 9.91 |
| 06357 | C215-11 | 2.195 | 1.355 | Cet | −3 | 3.93 | 9.91 |
| 06358 | C215-1 | 1.110 | 0.590 | McC | −6 | 7.93 | 9.91 |
| 06359 | C215-2 | 1.523 | 0.928 | McC | −6 | 7.93 | 9.91 |
| 06360 | C215-3 | 0.165 | 0.064 | McC | −4 | 4.93 | 9.91 |
| 06361 | C215-4 | 0.315 | 0.135 | McC | −3 | 3.93 | 9.91 |
| 06362 | C215-5 | 0.980 | 0.720 | McC | −3 | 3.93 | 9.91 |
| 07074 | C43-1 | 1.5825 | 1.3675 | McC | −6 | 7.26 | 9.66 |
| 07075 | C44-1 | 0.1822 | 0.0755 | McC | −5 | 6.01 | 9.91 |
| 07076 | C44-2 | 0.5950 | 0.3350 | McC | −5 | 6.01 | 9.91 |
| 07077 | C44-3 | 0.1432 | 0.0486 | McC | −4 | 5.01 | 9.91 |
| 07078 | C44-4 | 0.3086 | 0.1764 | McC | −4 | 5.01 | 9.91 |
| 07081 | C44-9 | 0.5525 | 0.2675 | Cet | −2 | 3.01 | 9.91 |
| 07082 | C45-1 | 0.4675 | 0.0925 | McC | −5 | 5.94 | 9.46 |
| 07086 | C45-9 | 0.2110 | 0.0842 | Cet | −2 | 2.94 | 9.46 |
| 07093 | C50-2 | 1.3125 | 0.9375 | McC | −5 | 5.99 | 7.69 |
| 07035 | C66-2 | 0.6475 | 0.3125 | McC | −7 | 8.01 | 9.53 |
| 07045 | C71-1 | 0.2079 | 0.1226 | McC | −5 | 5.95 | 10.58 |
| 07046 | C71-2 | 0.2030 | 0.0719 | McC | −4 | 4.95 | 10.58 |
| 07048 | C71-5 | 0.2388 | 0.1382 | Cet | −2 | 2.95 | 10.58 |
| 07051 | C100-11A | 0.6325 | 0.3425 | MRS | −4 | 5.07 | 10.47 |
| 07003 | C112-4 | 0.2513 | 0.0861 | McC | −5 | 6.14 | 10.88 |
| 07006 | C112-10 | 0.8913 | 0.1863 | Cet | −2 | 3.14 | 10.88 |
| 07022 | C121-8 | 0.1903 | 0.0448 | Cet | −5 | 6.14 | 10.88 |
| 07101 | C55-1 | 0.678 | 0.022 | McC | −6 | 6.95 | 10.38 |
| 07103 | C55-3 | 9.175 | 2.775 | McC | −5 | 5.95 | 10.38 |
| 07107 | C55-8A | 4.425 | 0.075 | Cet | −2 | 2.95 | 10.38 |
| 07111 | C60-1 | 0.232 | 0.028 | McC | −6 | 6.84 | 8.20 |
| 07113 | C60-3 | 0.340 | 0.105 | McC | −4 | 4.84 | 8.20 |
| 07126 | C231-1 | 0.323 | 0.097 | McC | −7 | 7.94 | 10.62 |
| 07127 | C231-2 | 0.141 | 0.030 | McC | −6 | 6.94 | 10.62 |
| 07128 | C231-5 | 0.365 | 0.095 | Cet | −3 | 3.94 | 10.62 |
| 07134 | C233-1 | 0.645 | 0.090 | McC | −3 | 3.98 | 6.18 |
| 07135 | C233-3 | 1.510 | 0.390 | McC | −2 | 2.98 | 6.18 |
| 07136 | C233-2 | 2.090 | 0.260 | McC | −3 | 3.98 | 6.18 |
| 07137 | C233-11 | 1.108 | 0.168 | CSH | −3 | 3.98 | 6.18 |
| | | AIEC isolated from family members of CD patients | | | | | |
| 06066 | C22-9 | 0.2710 | 0.192 | CS ana | −7 | 7.94 | 10.12 |
| 06381 | C33-5 | 0.465 | 0.185 | Cet | −2 | 2.90 | 9.46 |
| 06258 | C35-5 | 0.873 | 0.428 | McC | −6 | 7.64 | 10.14 |
| 06086 | C41-7 | 0.1242 | 0.072 | Cet | −2 | 2.91 | 10.14 |
| 06384 | C47-2 | 0.180 | 0.010 | McC | −6 | 7.07 | 9.62 |
| 06386 | C47-4 | 0.121 | 0.047 | McC | −5 | 6.07 | 9.62 |

TABLE 1-continued

| | | AIEC strains | | | | | |
|---|---|---|---|---|---|---|---|
| Number | Reference | Invasion I-407 Mean (%) | Invasion I-407 SEM (%) | Culture Medium [1] | Dilution | Level of E. coli (log UFC/g) [2] | Total Count (logUFC/g) [3] |
| 06097 | C64-2 | 1.4550 | 1.029 | McC | −5 | 6.03 | 9.80 |
| 06099 | C64-5 | 0.1175 | 0.068 | Cet | −2 | 3.03 | 9.80 |
| 06100 | C64-6 | 1.1225 | 0.794 | Cet | −2 | 3.03 | 9.8 |
| 06006 | C81-1 | 0.2850 | 0.202 | McC | −5 | 5.96 | 9.64 |
| 06007 | C81-2 | 0.3200 | 0.226 | McC | −5 | 5.96 | 9.64 |
| 06016 | C85-1 | 0.7540 | 0.435 | McC | −7 | 8.01 | 10.16 |
| 06019 | C85-5 | 1.4775 | 1.045 | Cet | −2 | 3.01 | 10.16 |
| 06394 | C87-7 | 0.130 | 0.030 | MRS | −2 | 3.03 | 9.42 |
| 06020 | C92-1 | 0.1253 | 0.072 | McC | −5 | 6.09 | 9.64 |
| 06021 | C92-2 | 0.1678 | 0.097 | McC | −4 | 5.09 | 9.64 |
| 06022 | C92-4 | 0.1229 | 0.071 | McC | −2 | 3.09 | 9.64 |
| 06396 | C95-1 | 4.975 | 2.575 | McC | −6 | 7.1 | 9.75 |
| 06037 | C102-1 | 0.6767 | 0.391 | McC | −6 | 6.90 | 8.55 |
| 06040 | C102-7 | 0.2342 | 0.135 | CS ana | −6 | 6.9 | 8.55 |
| 06080 | C107-2 | 0.5050 | 0.357 | McC | −6 | 7.1 | 9.55 |
| 06042 | C107-3 | 0.1900 | 0.110 | McC | −6 | 7.1 | 9.55 |
| 06043 | C107-5 | 1.7600 | 1.245 | McC | −6 | 7.1 | 9.55 |
| 06045 | C107-10 | 0.1975 | 0.140 | Cet | −2 | 3.1 | 9.55 |
| 06046 | C108-2 | 0.3925 | 0.278 | McC | −6 | 7.12 | 10.54 |
| 06049 | C108-10 | 0.2425 | 0.171 | CS ana | −7 | 8.12 | 10.54 |
| 06057 | C133-1 | 0.2475 | 0.175 | McC | −6 | 6.98 | 10.49 |
| 06101 | C133-4 | 0.1809 | 0.090 | Cet | −2 | 2.98 | 10.49 |
| 06160 | C189-2 | 1.3483 | 0.778 | McC | −6 | 7.07 | 10.19 |
| 06164 | C189-16B | 0.3295 | 0.190 | CSH | −8 | 8.07 | 10.19 |
| 06176 | C191-4 | 0.3975 | 0.281 | McC | −5 | 5.96 | 10.34 |
| 06177 | C191-5 | 0.3185 | 0.225 | McC | −5 | 5.96 | 10.34 |
| 06293 | C207-6 | 0.175 | 0.111 | Cet | −2 | 2.93 | 10.13 |
| 06295 | C208-6 | 0.116 | 0.047 | Cet | −2 | 2.91 | 10.57 |
| 06301 | C211-1 | 0.285 | 0.242 | McC | −2 | 2.87 | 10.07 |
| 06329 | C218-2 | 0.649 | 0.439 | McC | −6 | 6.88 | 10.06 |
| 06338 | C218-13 | 0.208 | 0.047 | Cet | −5 | 5.88 | 10.06 |
| 06341 | C218-16 | 0.304 | 0.218 | Cet | −4 | 4.88 | 10.06 |
| 07064 | C225-1 | 0.1280 | 0.0058 | McC | −4 | 4.90 | 10.10 |
| 07065 | C225-2 | 0.8354 | 0.7146 | McC | −4 | 4.90 | 10.10 |
| 07066 | C225-5 | 0.9200 | 0.4150 | McC | −6 | 6.87 | 9.49 |
| 07067 | C225-6 | 1.0792 | 0.5977 | McC | −5 | 5.87 | 9.49 |
| 07068 | C226-1 | 0.1193 | 0.0334 | McC | −5 | 6.06 | 10.58 |
| 07073 | C227-4 | 0.2164 | 0.1568 | Cet | −2 | 2.88 | 10.06 |
| 07120 | C228-2 | 0.228 | 0.013 | McC | −2 | 3.17 | 9.72 |
| 07121 | C229-1 | 0.126 | 0.012 | McC | −5 | 6.06 | 9.50 |
| 07122 | C229-2 | 0.117 | 0.034 | McC | −4 | 5.06 | 9.50 |
| 07123 | C229-7 | 0.190 | 0.045 | Cet | −5 | 6.06 | 9.50 |
| 07131 | C232-5 | 0.190 | 0.122 | Cet | −2 | 2.98 | 9.60 |
| 07138 | C235-1 | 0.658 | 0.193 | McC | −5 | 6.02 | 9.42 |
| | | AIEC isolated from control subjects | | | | | |
| 06235 | C174-6 | 2.833 | 2.468 | Cet | −2 | 3.05 | 10.59 |
| 06242 | C177-1 | 0.251 | 0.175 | McC | −6 | 6.99 | 9.95 |
| 06103 | C177-13 | 0.1461 | 0.073 | CS ana | −7 | 7.99 | 9.95 |
| 06105 | C177-2 | 0.1571 | 0.079 | McC | −5 | 5.99 | 9.95 |
| 06106 | C178-23 | 0.4527 | 0.261 | CSH | −5 | 6.03 | 10.24 |
| 06108 | C179-7 | 0.1103 | 0.064 | Cet | −2 | 3.07 | 10.53 |
| 06142 | C181-5 | 1.1525 | 0.815 | Cet | −3 | 4.01 | 9.96 |
| 06143 | C183-12 | 0.2117 | 0.122 | CSH | −7 | 8.2 | 9.95 |
| 06121 | C183-2 | 0.1867 | 0.108 | McC | −4 | 5.2 | 9.95 |
| 06122 | C183-5 | 1.1025 | 0.780 | Cet | −2 | 3.20 | 9.95 |
| 06145 | C184-17 | 0.1095 | 0.077 | CSH | −5 | 6.09 | 9.64 |
| 06146 | C185-22 | 0.3933 | 0.227 | CSH | −5 | 5.88 | 9.88 |
| 06126 | C185-1 | 0.6050 | 0.428 | McC | −4 | 4.88 | 9.88 |
| 06135 | C185-2 | 0.4500 | 0.318 | McC | −5 | 5.88 | 9.88 |
| 06136 | C185-3 | 0.4875 | 0.345 | McC | −2 | 2.88 | 9.88 |
| 06137 | C185-6 | 0.3125 | 0.221 | Cet | −2 | 2.88 | 9.88 |
| 06127 | C186-1 | 0.1063 | 0.053 | McC | −6 | 6.86 | 10.04 |
| 06129 | C186-4 | 0.4700 | 0.332 | Cet | −3 | 3.86 | 10.04 |
| 06158 | C188-15 | 0.1052 | 0.061 | CS ana | −6 | 6.94 | 9.60 |
| 06196 | C192-11 | 0.508 | 0.279 | Cet | −2 | 2.92 | 9.44 |
| 06197 | C195-1 | 0.206 | 0.157 | McC | −5 | 5.95 | 9.72 |
| 06198 | C195-2 | 1.806 | 1.363 | McC | −4 | 4.95 | 9.72 |
| 06200 | C195-6 | 2.498 | 1.482 | Cet | −2 | 2.95 | 9.72 |
| 06201 | C196-1 | 0.218 | 0.105 | McC | −7 | 7.87 | 9.61 |
| 06204 | C196-4 | 0.307 | 0.163 | McC | −5 | 5.87 | 9.61 |
| 06212 | C197-1 | 3.133 | 1.438 | McC | −6 | 6.86 | 10.32 |
| 06213 | C197-2 | 0.445 | 0.042 | McC | −6 | 6.86 | 10.32 |
| 06216 | C197-6 | 0.886 | 0.782 | Cet | −2 | 2.86 | 10.32 |

TABLE 1-continued

AIEC strains

| Number | Reference | Invasion I-407 Mean (%) | Invasion I-407 SEM (%) | Culture Medium [1] | Dilution | Level of E. coli (log UFC/g) [2] | Total Count (logUFC/g) [3] |
|---|---|---|---|---|---|---|---|
| 06217 | C198-1 | 0.143 | 0.112 | McC | −6 | 7.07 | 10.03 |
| 06218 | C198-2 | 0.113 | 0.096 | McC | −6 | 7.07 | 10.03 |
| 06221 | C199-3 | 5.367 | 3.132 | McC | −4 | 5.06 | 9.79 |
| 06222 | C199-4 | 1.353 | 0.942 | McC | −3 | 4.06 | 9.79 |
| 06223 | C199-5 | 2.980 | 2.122 | McC | −3 | 4.06 | 9.79 |
| 06224 | C199-6 | 5.398 | 2.837 | McC | −3 | 4.06 | 9.79 |
| 06225 | C200-1 | 0.538 | 0.277 | McC | −3 | 4.06 | 9.79 |
| 07032 | C222-1 | 0.1038 | 0.0783 | McC | −6 | 7.14 | 10.88 |
| 07033 | C222-2 | 1.2425 | 0.6575 | McC | −6 | 7.14 | 10.88 |
| 07125 | C230-1 | 0.300 | 0.055 | McC | −5 | 6.0 | 10.2 |

[1] McC = McConkey Agar (bioMérieux)
Cet = Cetrimide Agar (bioMérieux)
CS ana = anaerobic Columbia blood agar
MRS = Man Rogosa Sharp Agar (Oxoid)
CSH = Columbia SH Agar
[2] The "level of E. coli" refers to the amount of the AIEC strain in the feces.
[3] "Total Count" refers to all bacterial species in feces.

CS ana culture medium has the following composition (per liter medium):
39 g of Columbia blood agar base (Oxoid)
5 g of glucose
0.3 g of cysteine chlorohydrate
5 g of agar
pH 7.0±0.2

The mixture is sterilized for 15 minutes at 121° C. Just before plating, 5% of horse blood is added.

CSH culture medium has the following composition (per liter medium):
39 g of Columbia blood agar base (Oxoid)
3 g of cysteine chlorohydrate
pH 6.8±0.2

The mixture is sterilized for 15 minutes at 121° C. Just before plating, 2 ml of sterile ammonium citrate solution (0.25 g/10 ml water) are added. After incubation, bacteria using cysteine (and releasing sulfide) result in black colonies on this medium.

Example 2

Phage Isolation

Phages were isolated from sewage water as follows: sewage water was filtered at 0.2 µm and mixed with an equal volume of 2× Luria-Bertani (LB) medium. This mixture was inoculated with a fresh culture of LF82 strain and incubated on a shaker at 37° C. overnight. Chloroform (¹/₁₀ volume) was added to the flask and placed on a shaker for one hour. The medium was centrifuged at 10,000 g for 10 min. 1 ml of the supernatant was collected and ¹/₁₀ vol. of chloroform was added. After a brief mix by vortex, the Eppendorf tube was centrifuged at 7,500 g for 5 min. To determine if phages were present in this extract, a drop (10 µl) of the supernatant was applied on an LB agar plate and allowed to dry. Using a platinum wire, the plate was streaked from the drop through the rest of the plate to isolate individual phages. 1 ml of a growing culture of LF82 strain was applied to cover the entire plate; the excess was removed and the plate was incubated at 37° C. overnight. One or two plaques were picked up and resuspended in 200 µl of SM buffer (10 mM TrisHCl pH7, NaCl 200 mM, gelatin 0.03%). 20 µl of chloroform was added in each tube and tubes were briefly mixed by vortex and centrifuged at 7,500 g for 5 min. 10 µl of the supernatant was applied on a LB plate and allowed to dry and the previous procedure was repeated at least three times. Once the majority of isolated plaques were homogenous, 10 µl of the last resuspended plaque were added to 1 ml of growing culture of LF82 strain at OD 0.1 at 600 nm. This culture tube was incubated at 37° C. for 2 to 4 hours until lysis occurred. After addition of ¹/₁₀ vol. of chloroform, the culture was transferred to an Eppendorf tube, centrifuged at 7,500 g for 5 min and cooled to 4° C., thereby obtaining the primary stock. Several dilutions of this stock were kept at 4° C. and used to infect a larger volume of culture in order to prepare larger amounts of phages. Seven (7) phages were obtained as follows:

vB_EcoM_LF82_P1 (herein before and after P1) deposited with the French National Collection of Microorganisms at the Institut Pasteur under Accession Number CNCM I-4694;

vB_EcoM_LF82_P2 (herein before and after P2) deposited with the French National Collection of Microorganisms at the Institut Pasteur under Accession Number CNCM I-4695;

vB_EcoM_LF82_P3 (herein before and after P3) deposited with the French National Collection of Microorganisms at the Institut Pasteur under Accession Number CNCM I-4696;

vB_EcoM_LF82_P4 (herein before and after P4) deposited with the French National Collection of Microorganisms at the Institut Pasteur under Accession Number CNCM I-4697;

vB_EcoM_LF82_P5 (herein before and after P5) deposited with the French National Collection of Microorganisms at the Institut Pasteur under Accession Number CNCM I-4698;

vB_EcoM_LF82_P6 (herein before and after P6) deposited with the French National Collection of Microorganisms at the Institut Pasteur under Accession Number CNCM I-4699; and vB_EcoM_LF82_P8 (herein before and after P8) deposited with the French National Collection of Microorganisms at the Institut Pasteur under Accession Number CNCM I-4700.

CLB_P2, deposited with the French National Collection of Microorganisms at the Institut Pasteur under Accession Number CNCM I-4675, and its isolation is described in detail in Maura et al. Environmental Microbiology (2012) 14(8), 1844-1854.

P1 to P6 phages belong to the wV8 bacteriophage family.
P8 belongs to the RB69 bacteriophage family.
CLB_P2 belongs to the JS98 bacteriophage family.

The classification into the wV8, RB69 and JS98 bacteriophage families was done based on the sequence of the major capsid protein.

Example 3

In Vitro Assays of the Infectivity of Bacteriophages in AIEC Strains

Plaque assay was carried out by contacting serial dilutions of bacteriophage solutions (from not diluted to $10^{-8}$ dilution) with a Petri dish which surface was covered by one bacterium. After overnight incubation at 37° C. plaques were counted. When the bacterium tested was the bacterial host (reference host) used to isolate bacteriophages it was considered that the plaque assay gave an efficiency of 100%. When the bacterium tested was not the original host, then the results were expressed by comparison to the reference host. A result greater than 80% (+++) means that the bacterium is a highly efficient host compared to the reference host, while a result between 0.1 and 80% (++) means that the bacterium is an efficient host, and a result below 0.1% (+) but above 0 means that the bacterium is a moderately efficient host, and finally 0 (−) means that the bacterium is totally resistant.

Results

Table 2 shows the result of the host spectrum of the 8 phages (as isolated/identified in Example 2) on 38 strains (out of the 166 strains isolated in Example 1, Table 1)

TABLE 2

Strains tested and effective efficiency of plating (EOP) obtained for each bacteriophage

| Bacterial Strain | P1 | P2 | P3 | P4 | P5 | P6 | P8 | CLB_P2 |
|---|---|---|---|---|---|---|---|---|
| LF82 | +++ | +++ | +++ | +++ | +++ | +++ | +++ | +++ |
| 06023 | − | − | − | − | − | − | − | ++ |
| 06030 | − | − | − | − | − | − | + | +++ |
| 06033 | ++ | ++ | ++ | ++ | ++ | ++ | + | +++ |
| 06066 | − | − | − | − | − | − | +++ | − |
| 06072 | − | − | − | − | − | − | + | ++ |
| 06073 | − | − | − | − | − | − | + | +++ |
| 06075 | +++ | +++ | +++ | +++ | +++ | +++ | + | ++ |
| 06088 | ++ | ++ | ++ | ++ | ++ | ++ | − | − |
| 06089 | ++ | ++ | ++ | ++ | ++ | ++ | − | − |
| 06122 | ++ | ++ | ++ | ++ | ++ | ++ | − | − |
| 06150 | − | − | − | − | − | − | + | − |
| 06351 | ++ | ++ | ++ | ++ | ++ | ++ | − | ++ |
| 06353 | + | + | + | + | + | + | − | − |
| 06354 | − | − | − | − | − | − | − | − |
| 06356 | ++ | + | + | + | + | + | − | − |
| 06357 | + | + | + | + | + | + | − | − |
| 06358 | ++ | + | + | + | + | + | − | − |
| 06359 | ++ | + | + | + | + | + | − | − |
| 06361 | + | ++ | + | + | + | + | + | − |
| 06362 | − | − | − | − | − | − | − | − |
| 07045 | − | − | − | − | − | − | − | − |
| 07046 | − | − | − | − | − | − | − | ++ |
| 07048 | − | − | − | − | − | − | − | − |
| 07051 | − | − | − | − | − | − | − | − |
| 07075 | − | − | − | − | − | − | − | − |
| 07076 | ++ | +++ | ++ | + | + | + | +++ | ++ |
| 07077 | − | − | − | − | − | − | − | − |
| 07078 | ++ | +++ | + | + | + | + | + | ++ |
| 07081 | ++ | +++ | ++ | + | + | ++ | +++ | ++ |
| 07082 | +++ | +++ | +++ | +++ | +++ | +++ | +++ | ++ |
| 07107 | +++ | ++ | +++ | ++ | +++ | +++ | − | +++ |
| 07126 | +++ | +++ | +++ | +++ | +++ | +++ | − | ++ |
| 07127 | +++ | ++ | +++ | +++ | ++ | ++ | − | ++ |
| 07128 | − | − | − | − | − | − | − | ++ |
| 07134 | − | − | − | − | − | − | − | − |
| 07135 | − | − | − | − | − | − | − | ++ |
| 07136 | − | − | − | − | − | − | − | − |
| 07137 | − | − | − | − | − | − | ++ | − |

TABLE 3 number of strains infected by phages:

| Efficacy | P1 | P2 | P3 | P4 | P5 | P6 | P8 | CLB_P2 |
|---|---|---|---|---|---|---|---|---|
| + | 3 | 5 | 6 | 9 | 9 | 8 | 8 | 0 |
| ++ | 10 | 8 | 8 | 6 | 6 | 7 | 1 | 13 |
| +++ | 5 | 6 | 5 | 4 | 4 | 4 | 4 | 5 |
| Total/38 | 18 | 19 | 19 | 19 | 19 | 19 | 13 | 18 |

Numbers indicate the number of strains infected by one bacteriophage

Example 4

In Vivo Replication of Bacteriophages in the Gut of Mice

In vivo replication of bacteriophages in the gut of mice was evaluated as follows: First, the strain LF82 was engineered to carry two antibiotic resistance genes conferring respectively resistance to Streptomycin and Kanamycin. This new bacterial strain was named LF82SK and its invasive properties were verified as to be similar to the original LF82 strain.

Three (3) groups of two (2) mice each:

Group 1: non-colonized mice+phages
Group 2: LF82SK colonized mice
Group 3: LF82SK colonized mice+phages Streptomycin (5 g/L) was added to drinking water of all animals 3 days before day 0 and kept along the experiment.

At day 0, LF82SK was administered to Group 2 and 3 in order to allow the strain to colonize mice's gut.

At day 4, 200 µl of a cocktail of P2+P6 bacteriophages was administered to Group 1 and 3 (gavage solution $10^8$ pfu/ml) once in the morning and once in the afternoon. P2+P6 bacteriophages were also added to the drinking water ($10^8$ pfu/ml). At day 5 in the morning, mice were sacrificed to evaluate the number of bacteria and bacteriophages in the ileum and in the feces.

Results:

Bacteria (*E. coli*):

Group 1: no bacteria;
Group 2: in ileum—$10^6$ cfu/g organ; in feces—$10^8$ cfu/organ;
Group 3: in ileum and feces: bacteria all lysed by phages.

Phages:
  Group 1: in ileum—$10^6$ pfu/g organ; in feces—$10^7$ pfu/organ;
  Group 2: no phages
  Group 3: in ileum—$10^6$ pfu/g organ; in feces—$10^{10}$ pfu/organ;
In the feces, there were 100 times more phages in Group 3 than in Group 1 showing the multiplication of the phages in vivo.

Example 5

In Vivo Replication of Bacteriophages In The Gut of Mice

In vivo replication of bacteriophages in the gut of mice was evaluated as follows:
12 mice were dispatched into three (3) groups of four (4) mice each:
  Group 1: non-colonized mice+phages
  Group 2: LF82SK-colonized mice
  Group 3: LF82SK-colonized mice+phages
Streptomycin (5 g/L) was added to drinking water of all animals 3 days before day 0 and kept along the experiment.
At day 0, LF82SK was given to mice of Group 2 and 3 in order to allow the strain to colonize mice's gut.
At day 4, bacteriophages (cocktail of P2+P6+P8 at $10^8$ pfu/mL each) were added in the drinking water of Group 1 and 3.
At day 5, mice were sacrificed to evaluate the number of bacteria and bacteriophages in the ileum and in the feces. 100 µl of ileal homogenates from the three groups were taken to extract whole DNA using Maxwell® 16 Tissue DNA purification kit from Promega.
  Results:
  Bacteria (*E. coli*):
  Group 1: no bacteria;
  Group 2: in ileum—$3.2 \cdot 10^6$ cfu/g of organ; in feces—$1.2 \cdot 10^9$ cfu/g of feces;
  Group 3: in ileum and feces: bacteria all lysed by phages.
  Phages:
  Group 1: in ileum—$1.4 \cdot 10^6$ pfu/g of organ; in feces—$5.2 \cdot 10^6$ pfu/g of feces;
  Group 2: no phages
  Group 3: in ileum—$2.6 \cdot 10^6$ pfu/g of organ; in feces—$1.0 \cdot 10^9$ pfu/g of feces;
In the feces, there were 200 times more phages in Group 3 than in Group 1 showing the multiplication of the phages in vivo.
DNA extracted from ileal sections was used to run quantitative PCR using two sets of primers. One set of primers (SEQ ID NO: 30-31) served to amplify DNA from "all bacteria" present in the sample while the second set (SEQ ID NO: 32-33) was used to amplify specifically DNA from "*E. coli*" bacteria. After normalization, results were expressed as the ratio of *E. coli* versus all bacteria.
  Group 1: qPCR amplifications were successful with all bacteria primers but not with *E. coli* primers. The ratio could not be calculated.
  Group 2: qPCR amplifications were successful with both set of primers. The average ratio was 0.6 (60% of total bacteria were *E. coli* bacteria)
  Group 3: qPCR amplifications were successful with both set of primers. The average ratio was 0.1 (10% of total bacteria were *E. coli* bacteria). Note that one mouse displayed a ratio of 0.4 while the three others displayed much lower values (0.06; 0.0002; 0.002).

In consequence bacteriophages were able to reduce the level of ileal colonization of LF82 bacteria by at least one order of magnitude in three mice out of four.

Example 6

In Vivo Assay of the Infectivity of Bacteriophages

Two cocktails of phages are selected for testing in wild-type (WT) mice and in CEACAM6 mice infected with the LF82 *E. coli* strain isolated from the CD patients.
In both WT mice and in CEACAM6 mice infected with the LF82 *E. coli* strain isolated from the CD patients, bacteriophages are administered to the mice by oral gavage in CMC. This kind of administration has many advantages: known quantity of bacteriophage administration and immediate gastric acidity neutralization. Phages are daily administered to the mice during the entire study.
  Mice are sacrificed at 5 days after LF82 administration.
  Main criteria: quantification of LF82 in ileal and colonic adherent flora of the mice.
  Minor criteria:
    Evaluation of weight
    Stool consistency.
    Presence of fecal blood (macro and bio)
  Luminal flora (conventional flora+LF82+phages)
    At sacrifice: Macroscopic and histologic examinations, adherent ileal and colonic flora+LF82+phages,
    At sacrifice: Macroscopic and histologic examinations, adherent ileal and colonic flora+LF82+phages,
  Biological parameters of inflammation are monitored, and bacteriophage translocation in the mesenteric lymph nodes (MLN), liver and spleen is searched for.
  Inflammation markers (MPO, pro-inflammatory cytokines IL-6, IL-12 and anti-inflammatory cytokines IL-10) are monitored. Bacteriophage and AIEC translocation in MLN, liver and spleen is searched for.
  Follow-up of bacteriophage elimination takes place in stools of mice receiving the bacteriophage cocktail without the LF82 strain.

Example 7

In Vivo Assay of a Cocktail of Phages on the LF82 Strain

In vivo replication of bacteriophages (cocktail of P2+P6+P8+CLB_P2) in the gut of mice was evaluated as follows:
20 mice were dispatched into two (2) groups of ten (10) mice each:
  Group 1: LF82SK-colonized mice
  Group 2: LF82SK-colonized mice+phages
Streptomycin (5 g/L) was added to drinking water of all animals 3 days before day 0 and kept along the experiment.
At day 0, LF82SK was given to mice of both groups in order to allow the strain to colonize mice's gut.
At day 3, bacteriophages (cocktail of P2+P6+P8+CLB_P2 at $10^8$ pfu/mL each) were given to mice of Group 2 by gavage.
At day 4 and 7, 5 mice of each group were sacrificed to evaluate the number of bacteria and bacteriophages in the ileum, in the colon and in the feces. 100 µl of ileal and colonic homogenates from the two groups were taken to extract whole DNA using Maxwell® 16 Tissue DNA purification kit from Promega.

Results:
Level of LF82 in stools:
At day 4 and 7 levels of LF82 were:
in group 1: 7 $10^9$; 1 $10^9$ cfu/g
in group 2: 8 $10^7$; 5 $10^8$ cfu/g
Level of Phages in stools:
At day 4 and 7 levels of Phages were:
in group 1: none
in group 2: 5 $10^9$; 6 $10^9$ pfu/g
In the presence of the phage cocktail the level of LF82 in stools was significantly lower than in their absence showing that the phage cocktail was able to infect LF82 inside mice's gut.
Level of LF82 in organs:
at day 4 levels of LF82 were:
in ileum of group 1: 100% of bacteria are *E. coli* (LF82)
in ileum of group 2: 20% of bacteria are *E. coli* (LF82)
in colon of group 1: 40% of bacteria are *E. coli* (LF82)
in colon of group 2: 2% of bacteria are *E. coli* (LF82)
at day 7 levels of LF82 were:
in ileum of group 1: 100% of bacteria are *E. coli* (LF82)
in ileum of group 2: 50% of bacteria are *E. coli* (LF82)
in colon of group 1: 25% of bacteria are *E. coli* (LF82)
in colon of group 2: 10% of bacteria are *E. coli* (LF82)
Level of Phages in organs:
at day 4 levels of Phages were:
in ileum of group 1: none
in ileum of group 2: 7 $10^8$ pfu/g
in colon of group 1: none
in colon of group 2: 5 $10^{10}$ pfu/g
at day 7 levels of LF82 were:
in ileum of group 1: none
in ileum of group 2: 7 $10^8$ pfu/g
in colon of group 1: none
in colon of group 4: 2 $10^8$ pfu/g
At day 2 and 5 the level of LF82 was reduced in both ileum and colon in the group treated by phages. This shows that phages infect LF82 in gut sections and not only in stools. Concomitantly, the level of phages at day 7 stays as high as at day 2 showing that phage can last several days in the gut after a unique initial administration.

Example 8

In Vivo Assay of the Infectivity of Bacteriophages

In vivo assay of the infectivity of bacteriophages (cocktail of P2+P6+P8) in CEACAM6 mice infected with LF82SK was evaluated as follows:
48 mice were dispatched into three (4) groups as follows:
Group 1: non-colonized mice (8 mice)
Group 2: non-colonized mice+phages (12 mice)
Group 3: LF82SK-colonized mice (16 mice)
Group 4: LF82SK-colonized mice+phages (12 mice)
DSS (dextran sulfate) 0.25% was introduced in the drinking water 3 days before day 0 and kept along the experiment.
Streptomycin (5 mg) was administrated by oral gavage to all animals 1 day before day 0.
At day 0, LF82SK was administered to mice of Group 3 and 4 in order to allow the strain to colonize mice's gut.
At day 1, phages (cocktail of P2+P6+P8 at $10^7$ pfu/mL each) were administered once to each mouse of Group 2 and 4 by oral gavage in CMC. This kind of administration has many advantages: known quantity of bacteriophage administration and immediate gastric acidity neutralization.

At day 1, 4 mice from Group 3 were sacrificed to evaluate the number of bacteria in the ileum, in the colon and in the feces before the administration of phages.
At day 2, respectively 4, 6, 6 and 6 mice from Groups 1, 2, 3 and 4 were sacrificed to evaluate the number of bacteria and bacteriophages in the ileum, in the colon and in the feces.
At day 5, respectively 4, 6, 6 and 6 mice from Groups 1, 2, 3 and 4 were sacrificed to evaluate the number of bacteria and bacteriophages in the ileum, in the colon and in the feces.
100 µl of ileal, colon and feces homogenates from the four groups were taken to extract whole DNA using Maxwell® 16 Tissue DNA purification kit from Promega. Weight, stool consistency and presence of fecal blood were monitored daily. DNA extracted from ileal sections was used to run quantitative PCR using one set of primers (SEQ ID NO: 44-45) to amplify a specific gene (pMT1) from LF82. Results were expressed as the number of copies of this gene per gram of tissues.

(SEQ ID NO: 44)
LF82 pMT1 F CCATTCATGCAGCAGCTCTTT (SEQ ID NO: 45)
LF82 pMT1 R ATCGGACAACATTAGCGGTGT

Results:
Values represent the median values obtained for each group of mice.
In group 1, neither LF82 nor Phages were detected along the experiment.
Level of LF82 in stools:
At day 1: the level of LF82 in Groups 3 and 4 were 5 $10^9$ and 6 $10^9$ cfu/g resp.
At day 2, 3 and 5 levels of LF82 were:
in group 3: 3 $10^9$; 5 $10^8$; 5 $10^7$ cfu/g
in group 4: 5 $10^5$; 5 $10^5$; 5 $10^3$ cfu/g
Level of Phages in stools:
At day 2, 3 and 5 levels of Phages were:
in group 2: 5 $10^5$ pfu/g; not detected; not detected
in group 4: 1 $10^9$; 1 $10^7$; 5 $10^6$ pfu/g
In the presence of phages the level of LF82 in stools was significantly lower than in their absence. Concomitantly, the level of phages was significantly higher in mice colonised by LF82 than in LF82-free mice. Both data confirmed that phages can infect LF82 in the gut.
Level of LF82 in organs:
at day 2 levels of LF82 were:
in ileum of group 3: 2 $10^6$ copies of pMT1/g
in ileum of group 4: 8 $10^4$ copies of pMT1/g
in colon of group 3: 2 $10^7$ copies of pMT1/g
in colon of group 4: 1 $10^5$ copies of pMT1/g
at day 5 levels of LF82 were:
in ileum of group 3: 5 $10^4$ copies of pMT1/g
in ileum of group 4: 8 $10^4$ copies of pMT1/g
in colon of group 3: 6 $10^6$ copies of pMT1/g
in colon of group 4: 2 $10^5$ copies of pMT1/g
Level of Phages in organs:
at day 2 levels of Phages were:
in ileum of group 2: not detected
in ileum of group 4: 8 $10^5$ pfu/g
in colon of group 2: 5 $10^4$ pfu/g
in colon of group 4: 5 $10^6$ pfu/g
at day 5 levels of LF82 were:
in ileum of group 2: not detected
in ileum of group 4: not detected in colon of group 2: not detected
in colon of group 4: 2 10$^4$ pfu/g At day 2, the level of LF82 was reduced in both ileum and colon in the group treated by phages. This shows that phages infected LF82 in gut sections and not only in stools.

Concomitantly, the level of phages was significantly higher in mice colonised by LF82 than in LF82-free mice.

At day 5, the level of LF82 in ileum was too weak to see a difference between the two groups while in colon samples the level of LF82 was still reduced in the group that received phages compared to the groups that did not. Concomitantly, we could only detect phages in colon of mice colonised by LF82. This shows that the effect of phages in reducing LF82 can last several days after the initial administration.

Despite high colonisation level of LF82 observed in this experiment, no sign of colitis was observed in any of the groups.

EMBODIMENTS

The present invention in particular relates to the following embodiments:

1. A pharmaceutical composition comprising:
   (i) at least one bacteriophage strain(s) capable of producing a lytic infection in an adherent-invasive *Escherichia coli* strain; and
   (ii) a pharmaceutically acceptable carrier;
   for use in the treatment of inflammatory bowel disease.
2. A composition according to embodiment 1 wherein the adherent-invasive *Escherichia coli* strain is present in one or more of the intestinal parts (small and large) of the subject.
3. A composition according to embodiment 1 wherein the adherent-invasive *Escherichia coli* strain is LF82, 07081, 07082, 07076 or 06075.
4. A composition according to any one of embodiments 1 to 3 wherein the inflammatory bowel disease is Crohn's disease or ulcerative colitis or recurrence of ileal lesions after surgery, for example surgery for the removal of at least a part of the small intestine in CD patients.
5. A composition according to any one of embodiments 1 to 4 wherein the composition comprises at least one of the bacteriophage strain P1 deposited with the French National Collection of Microorganisms at the Institut Pasteur under Accession Number CNCM I-4694 or a variant thereof, wherein the variant has the same lytic activity, preferably the same lytic activity and the same phenotypic characteristics as said bacteriophage strain P1, the bacteriophage strain P2 deposited with the French National Collection of Microorganisms at the Institut Pasteur under Accession Number CNCM I-4695 or a variant thereof, wherein the variant has the same lytic activity, preferably the same lytic activity and the same phenotypic characteristics as said bacteriophage strain P2, the bacteriophage strain P3 deposited with the French National Collection of Microorganisms at the Institut Pasteur under Accession Number CNCM I-4696 or a variant thereof, wherein the variant has the same lytic activity, preferably the same lytic activity and the same phenotypic characteristics as said bacteriophage strain P3, the bacteriophage strain P4 deposited with the French National Collection of Microorganisms at the Institut Pasteur under Accession Number CNCM I-4697 or a variant thereof, wherein the variant has the same lytic activity, preferably the same lytic activity and the same phenotypic characteristics as said bacteriophage strain P4, the bacteriophage strain P5 deposited with the French National Collection of Microorganisms at the Institut Pasteur under Accession Number CNCM I-4698 or a variant thereof, wherein the variant has the same lytic activity, preferably the same lytic activity and the same phenotypic characteristics as said bacteriophage strain P5, the bacteriophage strain P6 deposited with the French National Collection of Microorganisms at the Institut Pasteur under Accession Number CNCM I-4699 or a variant thereof, wherein the variant has the same lytic activity, preferably the same lytic activity and the same phenotypic characteristics as said bacteriophage strain P6, the bacteriophage strain P8 deposited with the French National Collection of Microorganisms at the Institut Pasteur under Accession Number CNCM I-4700 or a variant thereof, wherein the variant has the same lytic activity, preferably the same lytic activity and the same phenotypic characteristics as said bacteriophage strain P8 and the bacteriophage strain CLB_P2 deposited with the French National Collection of Microorganisms at the Institut Pasteur under Accession Number CNCM I-4675 or a variant thereof, wherein the variant has the same lytic activity, preferably the same lytic activity and the same phenotypic characteristics as said bacteriophage strain CLB_P2.
6. A composition according to any one of embodiments 1 to 5 wherein the composition is for oral administration.
7. Bacteriophage strain P1 deposited with the French National Collection of Microorganisms at the Institut Pasteur under Accession Number CNCM I-4694 or a variant thereof, wherein the variant has the same lytic activity, preferably the same lytic activity and the same phenotypic characteristics as said bacteriophage strain.
8. Bacteriophage strain P2 deposited with the French National Collection of Microorganisms at the Institut Pasteur under Accession Number CNCM I-4695 or a variant thereof, wherein the variant has the same lytic activity, preferably the same lytic activity and the same phenotypic characteristics as said bacteriophage strain.
9. Bacteriophage strain P3 deposited with the French National Collection of Microorganisms at the Institut Pasteur under Accession Number CNCM I-4696 or a variant thereof, wherein the variant has the same lytic activity, preferably the same lytic activity and the same phenotypic characteristics as said bacteriophage strain.
10. Bacteriophage strain P4 deposited with the French National Collection of Microorganisms at the Institut Pasteur under Accession Number CNCM I-4697 or a variant thereof, wherein the variant has the same lytic activity, preferably the same lytic activity and the same phenotypic characteristics as said bacteriophage strain.
11. Bacteriophage strain P5 deposited with the French National Collection of Microorganisms at the Institut Pasteur under Accession Number CNCM I-4698 or a variant thereof, wherein the variant has the same lytic activity, preferably the same lytic activity and the same phenotypic characteristics as said bacteriophage strain.
12. Bacteriophage strain P6 deposited with the French National Collection of Microorganisms at the Institut Pasteur under Accession Number CNCM I-4699 or a variant thereof, wherein the variant has the same lytic activity, preferably the same lytic activity and the same phenotypic characteristics as said bacteriophage strain.
13. Bacteriophage strain P8 deposited with the French National Collection of Microorganisms at the Institut Pasteur under Accession Number CNCM I-4700 or a variant thereof, wherein the variant has the same lytic activity, preferably the same lytic activity and the same phenotypic characteristics as said bacteriophage strain.

The invention claimed is:

1. A pharmaceutical composition comprising bacteriophages capable of producing a lytic infection in an adherent-invasive *Escherichia coli* strain, wherein the composition comprises:
   (a) bacteriophages of strain P2 deposited with the French National Collection of Microorganisms at the Institut Pasteur under Accession Number CNCM 1-4695, or a variant thereof, wherein the variant has the same lytic activity and at least 80% sequence identity on at least 70% of length as said deposited bacteriophage strain P2;
   (b) bacteriophages of strain P8 deposited with the French National Collection of Microorganisms at the Institut Pasteur under Accession Number CNCM 1-4700, or a variant thereof, wherein the variant has the same lytic activity and at least 80% sequence identity on at least 70% of length as said deposited bacteriophage strain P8;
   (c) bacteriophages of strain CLB P2 deposited with the French National Collection of Microorganisms at the Institut Pasteur under Accession Number CNCM 1-4675 or a variant thereof, wherein the variant has the same lytic activity as said deposited bacteriophage strain CLB P2, and
   (d) a pharmaceutically acceptable carrier comprising one or more pharmaceutically acceptable auxiliary agents selected from matrix-forming agents, thickeners, binders, lubricants, pH adjusting agents, protecting agents, viscosity enhancers, wicking agents, disintegrants, surfactants, anti-oxidants, wetting agents, colorants, flavoring agents, taste-masking agents, sweeteners, and preservatives.

2. The composition of claim 1, wherein the bacteriophages are lyophilized.

3. The composition of claim 1, formulated for administration by a route selected from oral, buccal, sublingual, rectal, nasal, topical, otic, vaginal, bronchial, pulmonary and parenteral.

4. The composition of claim 1, formulated for oral administration.

5. The composition of claim 1, formulated for oral administration in a dosage form selected from pills, tablets, dragees, capsules, powders, granules, solutions, and suspensions.

6. The composition of claim 1, formulated for rectal administration.

7. The composition of claim 1, formulated for rectal administration in a dosage form selected from suppositories and enemas.

8. The composition of claim 1, formulated in a dosage form comprising from $10^4$ to $10^{11}$ plaque forming units of said bacteriophages per dose.

9. The composition of claim 1, comprising:
   (a) bacteriophages of strain P2 deposited with the French National Collection of Microorganisms at the Institut Pasteur under Accession Number CNCM I-4695;
   (b) bacteriophages of strain P8 deposited with the French National Collection of Microorganisms at the Institut Pasteur under Accession Number CNCM I-4700; and
   (c) bacteriophages of strain CLB P2 deposited with the French National Collection of Microorganisms at the Institut Pasteur under Accession Number CNCM 1-4675.

10. The composition of claim 1, further comprising one or more bacteriophages selected from:
   bacteriophages of strain P1 deposited with the French National Collection of Microorganisms at the Institut Pasteur under Accession Number CNCM 1-4694, or a variant thereof, wherein the variant has the same lytic activity and at least 80% sequence identity on at least 70% of length as said deposited bacteriophage strain P1;
   bacteriophages of strain P3 deposited with the French National Collection of Microorganisms at the Institut Pasteur under Accession Number CNCM 1-4696, or a variant thereof, wherein the variant has the same lytic activity and at least 80% sequence identity on at least 70% of length as said deposited bacteriophage strain P3;
   bacteriophages of strain P4 deposited with the French National Collection of Microorganisms at the Institut Pasteur under Accession Number CNCM 1-4697, or a variant thereof, wherein the variant has the same lytic activity and at least 80% sequence identity on at least 70% of length as said deposited bacteriophage strain P4;
   bacteriophages of strain P5 deposited with the French National Collection of Microorganisms at the Institut Pasteur under Accession Number CNCM 1-4698, or a variant thereof, wherein the variant has the same lytic activity as and at least 80% sequence identity on at least 70% of length said deposited bacteriophage strain P5; and
   bacteriophages of strain P6 deposited with the French National Collection of Microorganisms at the Institut Pasteur under Accession Number CNCM 1-4699, or a variant thereof, wherein the variant has the same lytic activity and at least 80% sequence identity on at least 70% of length as said deposited bacteriophage strain P6.

* * * * *

SEQUENCE LISTING

<160> NUMBER OF SEQ ID NOS: 45

<210> SEQ ID NO 1
<211> LENGTH: 368
<212> TYPE: PRT
<213> ORGANISM: Bacteriophage wV8

<400> SEQUENCE: 1

Met Leu Thr Asn Ser Glu Lys Ser Arg Phe Phe Leu Ala Asp Leu Thr
1               5                   10                  15

Gly Glu Val Gln Ser Ile Pro Asn Thr Tyr Gly Tyr Ile Ser Asn Leu
            20                  25                  30

Gly Leu Phe Arg Ser Ala Pro Ile Thr Gln Thr Thr Phe Leu Met Asp
        35                  40                  45

Leu Thr Asp Trp Asp Val Ser Leu Leu Asp Ala Val Asp Arg Asp Ser
    50                  55                  60

Arg Lys Ala Glu Thr Ser Ala Pro Glu Arg Val Arg Gln Ile Ser Phe
65                  70                  75                  80

Pro Met Met Tyr Phe Lys Glu Val Glu Ser Ile Thr Pro Asp Glu Ile
                85                  90                  95

Gln Gly Val Arg Gln Pro Gly Thr Ala Asn Glu Leu Thr Thr Glu Ala
            100                 105                 110

Val Val Arg Ala Lys Lys Leu Met Lys Ile Arg Thr Lys Phe Asp Ile
        115                 120                 125

Thr Arg Glu Phe Leu Phe Met Gln Ala Leu Lys Gly Lys Val Val Asp
    130                 135                 140

Ala Arg Gly Thr Leu Tyr Ala Asp Leu Tyr Lys Gln Phe Asp Val Glu
145                 150                 155                 160

Lys Lys Thr Val Tyr Phe Asp Leu Asp Asn Pro Asn Ala Asp Ile Asp
                165                 170                 175

Ala Ala Ile Glu Glu Leu Arg Met His Met Glu Asp Glu Ala Lys Thr
            180                 185                 190

Gly Thr Val Ile Asn Gly Glu Glu Ile His Val Val Asp Arg Leu
        195                 200                 205

Phe Phe Ser Lys Leu Val Lys His Pro Lys Ile Arg Asp Ala Tyr Leu
    210                 215                 220

Ala Gln Gln Thr Pro Leu Ala Trp Gln Gln Ile Thr Gly Ser Leu Arg
225                 230                 235                 240

Thr Gly Gly Thr Asp Gly Val Gln Ala His Met Asn Thr Phe Tyr Tyr
                245                 250                 255

Gly Gly Val Lys Phe Val Gln Tyr Asn Gly Lys Phe Lys Asp Lys Arg
            260                 265                 270

Gly Lys Val His Thr Leu Val Ser Ile Asp Ser Val Ala Ala Thr Val
        275                 280                 285

Gly Val Gly His Ala Phe Pro Asn Val Ser Met Leu Gly Glu Ala Asn
    290                 295                 300

Asn Ile Phe Glu Val Ala Tyr Gly Pro Cys Pro Lys Met Gly Tyr Ala
305                 310                 315                 320

Asn Thr Leu Gly Gln Glu Leu Tyr Val Phe Glu Tyr Glu Lys Asp Arg
                325                 330                 335

Asp Glu Gly Ile Asp Phe Glu Ala His Ser Tyr Met Leu Pro Tyr Cys
            340                 345                 350

Thr Arg Pro Gln Leu Leu Val Asp Val Arg Ser Asp Ala Lys Pro Asp
        355                 360                 365

<210> SEQ ID NO 2
<211> LENGTH: 27
<212> TYPE: PRT
<213> ORGANISM: Artificial Sequence
<220> FEATURE:
<223> OTHER INFORMATION: Peptide from bacteriophage strain P1 aligning
      with position 10-36 of the major capsid protein of bacteriophage
      wV8 (SEQ ID NO: 1)

<400> SEQUENCE: 2

Phe Phe Leu Ala Asp Leu Thr Gly Glu Val Gln Ser Ile Pro Asn Thr
1               5                   10                  15

Tyr Gly Tyr Ile Ser Asn Leu Gly Leu Phe Arg
            20                  25

<210> SEQ ID NO 3
<211> LENGTH: 55
<212> TYPE: PRT
<213> ORGANISM: Artificial Sequence
<220> FEATURE:
<223> OTHER INFORMATION: Peptide from bacteriophage strain P2 aligning
      with position 8-62 of the major capsid protein of bacteriophage
      wV8 (SEQ ID NO: 1)

<400> SEQUENCE: 3

Ser Arg Phe Phe Leu Ala Asp Leu Thr Gly Glu Val Gln Ser Ile Pro
1               5                   10                  15

Asn Thr Tyr Gly Tyr Ile Ser Asn Leu Gly Leu Phe Arg Ser Ala Pro
            20                  25                  30

Ile Thr Gln Thr Thr Phe Leu Met Asp Leu Thr Asp Trp Asp Val Ser
        35                  40                  45

Leu Leu Asp Ala Val Asp Arg
    50                  55

<210> SEQ ID NO 4
<211> LENGTH: 39
<212> TYPE: PRT
<213> ORGANISM: Artificial Sequence
<220> FEATURE:
<223> OTHER INFORMATION: Peptide from bacteriophage strain P1-P6
      aligning with position 77-115 of the major capsid protein of
      bacteriophage wV8 (SEQ ID NO: 1)

<400> SEQUENCE: 4

Gln Ile Ser Phe Pro Met Met Tyr Phe Lys Glu Val Glu Ser Ile Thr
1               5                   10                  15

Pro Asp Glu Ile Gln Gly Val Arg Gln Pro Gly Thr Ala Asn Glu Leu
            20                  25                  30

Thr Thr Glu Ala Val Val Arg
        35

<210> SEQ ID NO 5
<211> LENGTH: 16
<212> TYPE: PRT
<213> ORGANISM: Artificial Sequence
<220> FEATURE:
<223> OTHER INFORMATION: Peptide from bacteriophage strain P1-P6
      aligning with position 124-139 of the major capsid protein of
      bacteriophage wV8 (SEQ ID NO: 1)

<400> SEQUENCE: 5

Thr Lys Phe Asp Ile Thr Arg Glu Phe Leu Phe Met Gln Ala Leu Lys
1               5                   10                  15

```
<210> SEQ ID NO 6
<211> LENGTH: 9
<212> TYPE: PRT
<213> ORGANISM: Artificial Sequence
<220> FEATURE:
<223> OTHER INFORMATION: Peptide from bacteriophage strain P1-P5
      aligning with position 147-155 of the major capsid protein of
      bacteriophage wV8 (SEQ ID NO: 1)

<400> SEQUENCE: 6

Gly Thr Leu Tyr Ala Asp Leu Tyr Lys
1               5

<210> SEQ ID NO 7
<211> LENGTH: 15
<212> TYPE: PRT
<213> ORGANISM: Artificial Sequence
<220> FEATURE:
<223> OTHER INFORMATION: Peptide from bacteriophage strain P6 aligning
      with position 147-161 of the major capsid protein of bacteriophage
      wV8 (SEQ ID NO: 1)

<400> SEQUENCE: 7

Gly Thr Leu Tyr Ala Asp Leu Tyr Lys Gln Phe Asp Val Glu Lys
1               5                   10                  15

<210> SEQ ID NO 8
<211> LENGTH: 22
<212> TYPE: PRT
<213> ORGANISM: Artificial Sequence
<220> FEATURE:
<223> OTHER INFORMATION: Peptide from bacteriophage strain P1 aligning
      with position 162-183 of the major capsid protein of bacteriophage
      wV8 (SEQ ID NO: 1)

<400> SEQUENCE: 8

Lys Thr Val Tyr Phe Asp Leu Asp Asn Pro Asn Ala Asp Ile Asp Ala
1               5                   10                  15

Ser Ile Glu Glu Leu Arg
            20

<210> SEQ ID NO 9
<211> LENGTH: 21
<212> TYPE: PRT
<213> ORGANISM: Artificial Sequence
<220> FEATURE:
<223> OTHER INFORMATION: Peptide from bacteriophage strain P3 aligning
      with position 163-183 of the major capsid protein of bacteriophage
      wV8 (SEQ ID NO: 1)

<400> SEQUENCE: 9

Thr Val Tyr Phe Asp Leu Asp Asn Pro Asn Ala Asp Ile Asp Ala Ser
1               5                   10                  15

Ile Glu Glu Leu Arg
            20

<210> SEQ ID NO 10
<211> LENGTH: 21
<212> TYPE: PRT
<213> ORGANISM: Artificial Sequence
<220> FEATURE:
<223> OTHER INFORMATION: Peptide from bacteriophage strain P5-P6
      aligning with position 163-183 of the major capsid protein of
      bacteriophage wV8 (SEQ ID NO: 1)

<400> SEQUENCE: 10

Thr Ile Tyr Phe Asp Leu Asp Asn Pro Asn Ala Asp Ile Asp Ala Ser
1               5                   10                  15
```

Ile Glu Glu Leu Arg
            20

<210> SEQ ID NO 11
<211> LENGTH: 16
<212> TYPE: PRT
<213> ORGANISM: Artificial Sequence
<220> FEATURE:
<223> OTHER INFORMATION: Peptide from bacteriophage strain P1 and P3-P6
      aligning with position 192-207 of the major capsid protein of
      bacteriophage wV8 (SEQ ID NO: 1)

<400> SEQUENCE: 11

Thr Gly Thr Val Ile Asn Gly Glu Glu Ile His Val Val Val Asp Arg
1               5                   10                  15

<210> SEQ ID NO 12
<211> LENGTH: 21
<212> TYPE: PRT
<213> ORGANISM: Artificial Sequence
<220> FEATURE:
<223> OTHER INFORMATION: Peptide from bacteriophage strain P2 aligning
      with position 192-212 of the major capsid protein of bacteriophage
      wV8 (SEQ ID NO: 1)

<400> SEQUENCE: 12

Thr Gly Thr Val Ile Asn Gly Glu Glu Ile His Val Val Val Asp Arg
1               5                   10                  15

Leu Phe Phe Ser Lys
            20

<210> SEQ ID NO 13
<211> LENGTH: 22
<212> TYPE: PRT
<213> ORGANISM: Artificial Sequence
<220> FEATURE:
<223> OTHER INFORMATION: Peptide from bacteriophage strain P1 aligning
      with position 219-240 of the major capsid protein of bacteriophage
      wV8 (SEQ ID NO: 1)

<400> SEQUENCE: 13

Ile Arg Asp Ala Tyr Leu Ala Gln Gln Thr Pro Leu Ala Trp Gln Gln
1               5                   10                  15

Ile Thr Gly Ser Leu Arg
            20

<210> SEQ ID NO 14
<211> LENGTH: 49
<212> TYPE: PRT
<213> ORGANISM: Artificial Sequence
<220> FEATURE:
<223> OTHER INFORMATION: Peptide from bacteriophage strain P2 aligning
      with position 219-267 of the major capsid protein of bacteriophage
      wV8 (SEQ ID NO: 1)

<400> SEQUENCE: 14

Ile Arg Asp Ala Tyr Leu Ala Gln Gln Thr Pro Leu Ala Trp Gln Gln
1               5                   10                  15

Ile Thr Gly Ser Leu Arg Thr Gly Gly Thr Asp Gly Val Gln Ala His
            20                  25                  30

Met Asn Thr Phe Tyr Tyr Gly Gly Val Lys Phe Val Gln Tyr Asn Gly
        35                  40                  45

Lys

```
<210> SEQ ID NO 15
<211> LENGTH: 20
<212> TYPE: PRT
<213> ORGANISM: Artificial Sequence
<220> FEATURE:
<223> OTHER INFORMATION: Peptide from bacteriophage strain P3-P4
      aligning with position 221-240 of the major capsid protein of
      bacteriophage wV8 (SEQ ID NO: 1)

<400> SEQUENCE: 15

Asp Ala Tyr Leu Ala Gln Gln Thr Pro Leu Ala Trp Gln Gln Ile Thr
1               5                   10                  15

Gly Ser Leu Arg
            20

<210> SEQ ID NO 16
<211> LENGTH: 47
<212> TYPE: PRT
<213> ORGANISM: Artificial Sequence
<220> FEATURE:
<223> OTHER INFORMATION: Peptide from bacteriophage strain P5 aligning
      with position 221-267 of the major capsid protein of bacteriophage
      wV8 (SEQ ID NO: 1)

<400> SEQUENCE: 16

Asp Ala Tyr Leu Ala Gln Gln Thr Pro Leu Ala Trp Gln Gln Ile Thr
1               5                   10                  15

Gly Ser Leu Arg Thr Gly Gly Ala Asp Gly Val Gln Ala His Met Asn
            20                  25                  30

Thr Phe Tyr Tyr Gly Gly Val Lys Phe Val Gln Tyr Asn Gly Lys
        35                  40                  45

<210> SEQ ID NO 17
<211> LENGTH: 40
<212> TYPE: PRT
<213> ORGANISM: Artificial Sequence
<220> FEATURE:
<223> OTHER INFORMATION: Peptide from bacteriophage strain P6 aligning
      with position 221-260 of the major capsid protein of bacteriophage
      wV8 (SEQ ID NO: 1)

<400> SEQUENCE: 17

Asp Ala Tyr Leu Ala Gln Gln Thr Pro Leu Ala Trp Gln Gln Ile Thr
1               5                   10                  15

Gly Ser Leu Arg Thr Gly Gly Ala Asp Gly Val Gln Ala His Met Asn
            20                  25                  30

Thr Phe Tyr Tyr Gly Gly Val Lys
        35                  40

<210> SEQ ID NO 18
<211> LENGTH: 7
<212> TYPE: PRT
<213> ORGANISM: Artificial Sequence
<220> FEATURE:
<223> OTHER INFORMATION: Peptide from bacteriophage strain P1, P3 and P4
      aligning with position 261-267 of the major capsid protein of
      bacteriophage wV8 (SEQ ID NO: 1)

<400> SEQUENCE: 18

Phe Val Gln Tyr Asn Gly Lys
1               5

<210> SEQ ID NO 19
<211> LENGTH: 20
<212> TYPE: PRT
<213> ORGANISM: Artificial Sequence
```

```
<220> FEATURE:
<223> OTHER INFORMATION: Peptide from bacteriophage strain P1-P2
      aligning with position 317-336 of the major capsid protein of
      bacteriophage wV8 (SEQ ID NO: 1)

<400> SEQUENCE: 19

Met Gly Tyr Ala Asn Thr Leu Gly Gln Glu Leu Tyr Val Phe Glu Tyr
1               5                   10                  15

Glu Lys Asp Arg
            20

<210> SEQ ID NO 20
<211> LENGTH: 8
<212> TYPE: PRT
<213> ORGANISM: Artificial Sequence
<220> FEATURE:
<223> OTHER INFORMATION: Peptide from bacteriophage strain P1-P6
      aligning with position 355-362 of the major capsid protein of
      bacteriophage wV8 (SEQ ID NO: 1)

<400> SEQUENCE: 20

Pro Gln Leu Leu Val Asp Val Arg
1               5

<210> SEQ ID NO 21
<211> LENGTH: 522
<212> TYPE: PRT
<213> ORGANISM: Bacteriophage RB69

<400> SEQUENCE: 21

Met Thr Thr Ile Lys Thr Lys Ala Gln Leu Val Asp Lys Trp Lys Glu
1               5                   10                  15

Leu Leu Glu Gly Glu Gly Leu Pro Glu Ile Ala Asn Ser Lys Gln Ala
                20                  25                  30

Ile Ile Ala Lys Ile Phe Glu Asn Gln Glu Lys Asp Phe Glu Val Ser
            35                  40                  45

Pro Glu Tyr Lys Asp Glu Lys Ile Ala Gln Ala Phe Gly Ser Phe Leu
        50                  55                  60

Thr Glu Ala Glu Ile Gly Gly Asp His Gly Tyr Asn Ala Gln Asn Ile
65                  70                  75                  80

Ala Ala Gly Gln Thr Ser Gly Ala Val Thr Gln Ile Gly Pro Ala Val
                85                  90                  95

Met Gly Met Val Arg Arg Ala Ile Pro Asn Leu Ile Ala Phe Asp Ile
                100                 105                 110

Cys Gly Val Gln Pro Met Asn Ser Pro Thr Gly Gln Val Phe Ala Leu
            115                 120                 125

Arg Ala Val Tyr Gly Lys Asp Pro Ile Ala Ala Gly Ala Lys Glu Ala
        130                 135                 140

Phe His Pro Met Tyr Ala Pro Asp Ala Met Phe Ser Gly Gln Gly Ala
145                 150                 155                 160

Ala Lys Lys Phe Pro Ala Leu Ala Ala Ser Thr Gln Thr Lys Val Gly
                165                 170                 175

Asp Ile Tyr Thr His Phe Phe Gln Glu Thr Gly Thr Val Tyr Leu Gln
                180                 185                 190

Ala Ser Ala Gln Val Thr Ile Ser Ser Ala Asp Asp Ala Ala Lys
            195                 200                 205

Leu Asp Ala Glu Ile Ile Lys Gln Met Glu Ala Gly Ala Leu Val Glu
        210                 215                 220

Ile Ala Glu Gly Met Ala Thr Ser Ile Ala Glu Leu Gln Glu Gly Phe
```

```
                225                 230                 235                 240
Asn Gly Ser Thr Asp Asn Pro Trp Asn Glu Met Gly Phe Arg Ile Asp
                    245                 250                 255
Lys Gln Val Ile Glu Ala Lys Ser Arg Gln Leu Lys Ala Ala Tyr Ser
                260                 265                 270
Ile Glu Leu Ala Gln Asp Leu Arg Ala Val His Gly Met Asp Ala Asp
            275                 280                 285
Ala Glu Leu Ser Gly Ile Leu Ala Thr Glu Ile Met Leu Glu Ile Asn
290                 295                 300
Arg Glu Val Val Asp Trp Ile Asn Tyr Ser Ala Gln Val Gly Lys Ser
305                 310                 315                 320
Gly Met Thr Asn Ile Val Gly Ser Lys Ala Gly Val Phe Asp Phe Gln
                325                 330                 335
Asp Pro Ile Asp Ile Arg Gly Ala Arg Trp Ala Gly Glu Ser Phe Lys
                340                 345                 350
Ala Leu Leu Phe Gln Ile Asp Lys Glu Ala Val Glu Ile Ala Arg Gln
            355                 360                 365
Thr Gly Arg Gly Glu Gly Asn Phe Ile Ile Ala Ser Arg Asn Val Val
370                 375                 380
Asn Val Leu Ala Ser Val Asp Thr Gly Ile Ser Tyr Ala Ala Gln Gly
385                 390                 395                 400
Leu Ala Ser Gly Phe Asn Thr Asp Thr Thr Lys Ser Val Phe Ala Gly
                405                 410                 415
Val Leu Gly Gly Lys Tyr Arg Val Tyr Ile Asp Gln Tyr Ala Lys Gln
                420                 425                 430
Asp Tyr Phe Thr Val Gly Tyr Lys Gly Ala Asn Glu Met Asp Ala Gly
            435                 440                 445
Ile Tyr Tyr Ala Pro Tyr Val Ala Leu Thr Pro Leu Arg Gly Ser Asp
    450                 455                 460
Pro Lys Asn Phe Gln Pro Val Met Gly Phe Lys Thr Arg Tyr Gly Ile
465                 470                 475                 480
Gly Val Asn Pro Phe Ala Glu Ser Ser Leu Gln Ala Pro Gly Ala Arg
                485                 490                 495
Ile Gln Ser Gly Met Pro Ser Ile Leu Asn Ser Leu Gly Lys Asn Ala
            500                 505                 510
Tyr Phe Arg Arg Val Tyr Val Lys Gly Ile
            515                 520
```

<210> SEQ ID NO 22
<211> LENGTH: 20
<212> TYPE: PRT
<213> ORGANISM: Artificial Sequence
<220> FEATURE:
<223> OTHER INFORMATION: Peptide from bacteriophage strain P8 aligning
      with position 143-162 of the major capsid protein of bacteriophage
      RB69 (SEQ ID NO: 21)

<400> SEQUENCE: 22

```
Glu Ala Phe His Pro Met Tyr Ala Pro Asp Ala Met Phe Ser Gly Gln
1               5                   10                  15

Gly Ala Ala Lys
            20
```

<210> SEQ ID NO 23
<211> LENGTH: 12
<212> TYPE: PRT
<213> ORGANISM: Artificial Sequence

```
<220> FEATURE:
<223> OTHER INFORMATION: Peptide from bacteriophage strain P8 aligning
      with position 269-280 of the major capsid protein of bacteriophage
      RB69 (SEQ ID NO: 21)

<400> SEQUENCE: 23

Ala Ala Tyr Ser Ile Glu Leu Ala Gln Asp Leu Arg
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Peptide from bacteriophage strain P8 aligning
      with position 306-319 of the major capsid protein of bacteriophage
      RB69 (SEQ ID NO: 21)

<400> SEQUENCE: 24

Glu Val Val Asp Trp Ile Asn Tyr Ser Ala Gln Val Gly Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Peptide from bacteriophage strain P8 aligning
      with position 330-342 of the major capsid protein of bacteriophage
      RB69 (SEQ ID NO: 21)

<400> SEQUENCE: 25

Ala Gly Val Phe Asp Phe Gln Asp Pro Ile Asp Ile Arg
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Peptide from bacteriophage strain P8 aligning
      with position 346-352 of the major capsid protein of bacteriophage
      RB69 (SEQ ID NO: 21)

<400> SEQUENCE: 26

Trp Ala Gly Glu Ser Phe Lys
1               5

<210> SEQ ID NO 27
<211> LENGTH: 14
<212> TYPE: PRT
<213> ORGANISM: Artificial Sequence
<220> FEATURE:
<223> OTHER INFORMATION: Peptide from bacteriophage strain P8 aligning
      with position 368-381 of the major capsid protein of bacteriophage
      RB69 (SEQ ID NO: 21)

<400> SEQUENCE: 27

Gln Thr Gly Arg Gly Glu Gly Asn Phe Ile Ile Ala Ser Arg
1               5                   10

<210> SEQ ID NO 28
<211> LENGTH: 50
<212> TYPE: PRT
<213> ORGANISM: Artificial Sequence
<220> FEATURE:
<223> OTHER INFORMATION: Peptide from bacteriophage strain P8 aligning
      with position 412-461 of the major capsid protein of bacteriophage
      RB69 (SEQ ID NO: 21)
```

<400> SEQUENCE: 28

Ser Val Phe Ala Gly Val Leu Gly Gly Lys Tyr Arg Val Tyr Ile Asp
1               5                   10                  15

Gln Tyr Ala Lys Gln Asp Tyr Phe Thr Val Gly Tyr Lys Gly Ala Asn
            20                  25                  30

Glu Met Asp Ala Gly Ile Tyr Tyr Ala Pro Tyr Val Ala Leu Thr Pro
        35                  40                  45

Leu Arg
    50

<210> SEQ ID NO 29
<211> LENGTH: 44
<212> TYPE: PRT
<213> ORGANISM: Artificial Sequence
<220> FEATURE:
<223> OTHER INFORMATION: Peptide from bacteriophage strain P8 aligning
      with position 467-510 of the major capsid protein of bacteriophage
      RB69 (SEQ ID NO: 21)

<400> SEQUENCE: 29

Asn Phe Gln Pro Val Met Gly Phe Lys Thr Arg Tyr Gly Ile Gly Val
1               5                   10                  15

Asn Pro Phe Ala Glu Ser Ser Leu Gln Ala Pro Gly Ala Arg Ile Gln
            20                  25                  30

Ser Gly Met Pro Ser Ile Leu Asn Ser Leu Gly Lys
        35                  40

<210> SEQ ID NO 30
<211> LENGTH: 18
<212> TYPE: DNA
<213> ORGANISM: Artificial Sequence
<220> FEATURE:
<223> OTHER INFORMATION: All bacteria 16S gene forward primer

<400> SEQUENCE: 30
cggtgaatac gttcccgg                                                 18

<210> SEQ ID NO 31
<211> LENGTH: 22
<212> TYPE: DNA
<213> ORGANISM: Artificial Sequence
<220> FEATURE:
<223> OTHER INFORMATION: All bacteria 16S gene reverse primer

<400> SEQUENCE: 31
tacggctacc ttgttacgac tt                                            22

<210> SEQ ID NO 32
<211> LENGTH: 20
<212> TYPE: DNA
<213> ORGANISM: Artificial Sequence
<220> FEATURE:
<223> OTHER INFORMATION: E. coli 16S gene forward primer

<400> SEQUENCE: 32
catgccgcgt gtatgaagaa                                               20

<210> SEQ ID NO 33
<211> LENGTH: 21
<212> TYPE: DNA
<213> ORGANISM: Artificial Sequence
<220> FEATURE:
<223> OTHER INFORMATION: E. coli 16S gene reverse primer

<400> SEQUENCE: 33
cgggtaacgt caatgagcaa a                                    21

<210> SEQ ID NO 34
<211> LENGTH: 519
<212> TYPE: PRT
<213> ORGANISM: Bacteriophage JS98

<400> SEQUENCE: 34

```
Met Lys Lys Asn Ala Leu Val Gln Lys Trp Ser Ala Leu Leu Glu Asn
1               5                   10                  15

Glu Ala Leu Pro Glu Ile Val Gly Ala Ser Lys Gln Ala Ile Ile Ala
            20                  25                  30

Lys Ile Phe Glu Asn Gln Glu Gln Asp Ile Leu Thr Ala Pro Glu Tyr
        35                  40                  45

Arg Asp Glu Lys Ile Ser Glu Ala Phe Gly Ser Phe Leu Thr Glu Ala
    50                  55                  60

Glu Ile Gly Gly Asp His Gly Tyr Asp Ala Thr Asn Ile Ala Ala Gly
65                  70                  75                  80

Gln Thr Ser Gly Ala Val Thr Gln Ile Gly Pro Ala Val Met Gly Met
                85                  90                  95

Val Arg Arg Ala Ile Pro His Leu Ile Ala Phe Asp Ile Cys Gly Val
            100                 105                 110

Gln Pro Leu Asn Asn Pro Thr Gly Gln Val Phe Ala Leu Arg Ala Val
        115                 120                 125

Tyr Gly Lys Asp Pro Ile Ala Ala Gly Ala Lys Glu Ala Phe His Pro
    130                 135                 140

Met Tyr Ala Pro Asn Ala Met Phe Ser Gly Gln Gly Ala Ala Glu Thr
145                 150                 155                 160

Phe Glu Ala Leu Ala Ala Ser Lys Val Leu Glu Val Gly Lys Ile Tyr
                165                 170                 175

Ser His Phe Phe Glu Ala Thr Gly Ser Ala His Phe Gln Ala Val Glu
            180                 185                 190

Ala Val Thr Val Asp Ala Gly Ala Thr Asp Ala Ala Lys Leu Asp Ala
        195                 200                 205

Ala Val Thr Ala Leu Val Glu Ala Gly Gln Leu Ala Glu Ile Ala Glu
    210                 215                 220

Gly Met Ala Thr Ser Ile Ala Glu Leu Gln Glu Gly Phe Asn Gly Ser
225                 230                 235                 240

Thr Asp Asn Pro Trp Asn Glu Met Gly Phe Arg Ile Asp Lys Gln Val
                245                 250                 255

Ile Glu Ala Lys Ser Arg Gln Leu Lys Ala Ser Tyr Ser Ile Glu Leu
            260                 265                 270

Ala Gln Asp Leu Arg Ala Val His Gly Met Asp Ala Asp Ala Glu Leu
        275                 280                 285

Ser Gly Ile Leu Ala Thr Glu Ile Met Leu Glu Ile Asn Arg Glu Val
    290                 295                 300

Ile Asp Trp Ile Asn Tyr Ser Ala Gln Val Gly Lys Ser Gly Met Thr
305                 310                 315                 320

Asn Thr Val Gly Ala Lys Ala Gly Val Phe Asp Phe Gln Asp Pro Ile
                325                 330                 335

Asp Ile Arg Gly Ala Arg Trp Ala Gly Glu Ser Phe Lys Ala Leu Leu
            340                 345                 350
```

```
Phe Gln Ile Asp Lys Glu Ala Ala Glu Ile Ala Arg Gln Thr Gly Arg
            355                 360                 365

Gly Ala Gly Asn Phe Ile Ile Ala Ser Arg Asn Val Val Asn Val Leu
    370                 375                 380

Ala Ala Val Asp Thr Ser Val Ser Tyr Ala Ala Gln Gly Leu Gly Gln
385                 390                 395                 400

Gly Phe Asn Val Asp Thr Thr Lys Ala Val Phe Ala Gly Val Leu Gly
                405                 410                 415

Gly Lys Tyr Arg Val Tyr Ile Asp Gln Tyr Ala Arg Ser Asp Tyr Phe
            420                 425                 430

Thr Ile Gly Tyr Lys Gly Ser Asn Glu Met Asp Ala Gly Ile Tyr Tyr
        435                 440                 445

Ala Pro Tyr Val Ala Leu Thr Pro Leu Arg Gly Ser Asp Pro Lys Asn
    450                 455                 460

Phe Gln Pro Val Met Gly Phe Lys Thr Arg Tyr Gly Ile Gly Ile Asn
465                 470                 475                 480

Pro Phe Ala Asp Pro Ala Ala Gln Ala Pro Thr Lys Arg Ile Gln Asn
                485                 490                 495

Gly Met Pro Asp Ile Val Asn Ser Leu Gly Leu Asn Gly Tyr Phe Arg
            500                 505                 510

Arg Val Tyr Val Lys Gly Ile
            515

<210> SEQ ID NO 35
<211> LENGTH: 13
<212> TYPE: PRT
<213> ORGANISM: Artificial Sequence
<220> FEATURE:
<223> OTHER INFORMATION: Peptide from bacteriophage strain CLB_P2
      aligning with position 127-139 of the major capsid protein of
      bacteriophage JS98 (SEQ ID NO: 34)

<400> SEQUENCE: 35

Ala Val Tyr Gly Lys Asp Pro Ile Ala Ala Gly Ala Lys
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Peptide from bacteriophage strain CLB_P2
      aligning with position 266-277 of the major capsid protein of
      bacteriophage JS98 (SEQ ID NO: 34)

<400> SEQUENCE: 36

Ala Ser Tyr Ser Ile Glu Leu Ala Gln Asp Leu Arg
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Peptide from bacteriophage strain CLB_P2
      aligning with position 303-316 of the major capsid protein of
      bacteriophage JS98 (SEQ ID NO: 34)

<400> SEQUENCE: 37

Glu Val Ile Asp Trp Ile Asn Tyr Ser Ala Gln Val Gly Lys
1               5                   10
```

```
<210> SEQ ID NO 38
<211> LENGTH: 13
<212> TYPE: PRT
<213> ORGANISM: Artificial Sequence
<220> FEATURE:
<223> OTHER INFORMATION: Peptide from bacteriophage strain CLB_P2
      aligning with position 327-339 of the major capsid protein of
      bacteriophage JS98 (SEQ ID NO: 34)

<400> SEQUENCE: 38

Ala Gly Val Phe Asp Phe Gln Asp Pro Ile Asp Ile Arg
1               5                   10

<210> SEQ ID NO 39
<211> LENGTH: 22
<212> TYPE: PRT
<213> ORGANISM: Artificial Sequence
<220> FEATURE:
<223> OTHER INFORMATION: Peptide from bacteriophage strain CLB_P2
      aligning with position 343-364 of the major capsid protein of
      bacteriophage JS98 (SEQ ID NO: 34)

<400> SEQUENCE: 39

Trp Ala Gly Glu Ser Phe Lys Ala Leu Leu Phe Gln Ile Asp Lys Glu
1               5                   10                  15

Ala Ala Glu Ile Ala Arg
            20

<210> SEQ ID NO 40
<211> LENGTH: 10
<212> TYPE: PRT
<213> ORGANISM: Artificial Sequence
<220> FEATURE:
<223> OTHER INFORMATION: Peptide from bacteriophage strain CLB_P2
      aligning with position 369-378 of the major capsid protein of
      bacteriophage JS98 (SEQ ID NO: 34)

<400> SEQUENCE: 40

Gly Ala Gly Asn Phe Ile Ile Ala Ser Arg
1               5                   10

<210> SEQ ID NO 41
<211> LENGTH: 20
<212> TYPE: PRT
<213> ORGANISM: Artificial Sequence
<220> FEATURE:
<223> OTHER INFORMATION: Peptide from bacteriophage strain CLB_P2
      aligning with position 409-428 of the major capsid protein of
      bacteriophage JS98 (SEQ ID NO: 34)

<400> SEQUENCE: 41

Ala Val Phe Ala Gly Val Leu Gly Gly Lys Tyr Arg Val Tyr Ile Asp
1               5                   10                  15

Gln Tyr Ala Arg
            20

<210> SEQ ID NO 42
<211> LENGTH: 21
<212> TYPE: PRT
<213> ORGANISM: Artificial Sequence
<220> FEATURE:
<223> OTHER INFORMATION: Peptide from bacteriophage strain CLB_P2
      aligning with position 438-458 of the major capsid protein of
      bacteriophage JS98 (SEQ ID NO: 34)

<400> SEQUENCE: 42

Gly Ser Asn Glu Met Asp Ala Gly Ile Tyr Tyr Ala Pro Tyr Val Ala
1               5                   10                  15
```

```
Leu Thr Pro Leu Arg
            20

<210> SEQ ID NO 43
<211> LENGTH: 49
<212> TYPE: PRT
<213> ORGANISM: Artificial Sequence
<220> FEATURE:
<223> OTHER INFORMATION: Peptide from bacteriophage strain CLB_P2
      aligning with position 464-512 of the major capsid protein of
      bacteriophage JS98 (SEQ ID NO: 34)

<400> SEQUENCE: 43

Asn Phe Gln Pro Val Met Gly Phe Lys Thr Arg Tyr Gly Ile Gly Ile
1               5                   10                  15

Asn Pro Phe Ala Asp Pro Ala Ala Gln Ala Pro Thr Lys Arg Ile Gln
            20                  25                  30

Asn Gly Met Pro Asp Ile Val Asn Ser Leu Gly Leu Asn Gly Tyr Phe
        35                  40                  45

Arg

<210> SEQ ID NO 44
<211> LENGTH: 21
<212> TYPE: DNA
<213> ORGANISM: Artificial Sequence
<220> FEATURE:
<223> OTHER INFORMATION: forward primer to amplify a specific gene
      (pMT1) from LF82

<400> SEQUENCE: 44
ccattcatgc agcagctctt t                                           21

<210> SEQ ID NO 45
<211> LENGTH: 21
<212> TYPE: DNA
<213> ORGANISM: Artificial Sequence
<220> FEATURE:
<223> OTHER INFORMATION: reverse primer to amplify a specific gene
      (pMT1) from LF82

<400> SEQUENCE: 45
atcggacaac attagcggtg t                                           21
```